US00RE50172E

(19) United States
(12) Reissued Patent
Romero et al.

(10) Patent Number: US RE50,172 E
(45) Date of Reissued Patent: Oct. 15, 2024

(54) IN VITRO MATURATION OF A MAMMALIAN CUMULUS OOCYTE COMPLEX

(71) Applicant: Vrije Universiteit Brussel, Brussels (BE)

(72) Inventors: Sergio Romero, Brussels (BE); Flor Sanchez, Brussels (BE); Johan Smitz, Wemmel (BE)

(73) Assignee: Vrije Universiteit Brussel, Brussels (BE)

(21) Appl. No.: 17/459,555

(22) Filed: Aug. 27, 2021

Related U.S. Patent Documents

Reissue of:
(64) Patent No.: 10,392,601
Issued: Aug. 27, 2019
Appl. No.: 15/535,971
PCT Filed: Dec. 21, 2015
PCT No.: PCT/BE2015/000068
§ 371 (c)(1),
(2) Date: Jun. 14, 2017
PCT Pub. No.: WO2016/094970
PCT Pub. Date: Jun. 23, 2016

(30) Foreign Application Priority Data

Dec. 19, 2014 (BE) ..... 14199324.6

(51) Int. Cl.
*C12N 5/075* (2010.01)

(52) U.S. Cl.
CPC ..... *C12N 5/0609* (2013.01); *C12N 2500/25* (2013.01); *C12N 2501/11* (2013.01); *C12N 2501/19* (2013.01); *C12N 2501/31* (2013.01); *C12N 2501/392* (2013.01); *C12N 2501/998* (2013.01); *C12N 2517/10* (2013.01)

(58) Field of Classification Search
CPC ..... A61P 15/00; C12N 5/0609
See application file for complete search history.

(56) References Cited

U.S. PATENT DOCUMENTS 10,011,818 B2 * 7/2018 Tian ..... C12N 5/0609
2014/0314762 A1 * 10/2014 Cheng ..... A61K 38/22 424/134.1

FOREIGN PATENT DOCUMENTS

WO WO-03076600 A2 * 9/2003 ..... C12N 5/0609
WO WO2004035766 A2 4/2004
WO WO2005054449 A1 6/2005
WO WO2013013303 A1 1/2013

OTHER PUBLICATIONS

Sudiman et al. Plos One. Jul. 2014. vol. 9. Issue 7. pp. 1-11. (Year: 2014).*
Hussein et al. Developmental Biology. 296 (2006) 514-521. (Year: 2006).*
Franciosi et al. Biology of Reproduction (2014) 91 (3):61, 1-9 (Year: 2014).*
Blaha et al., "Cyclic guanosine monophosphate does not inhibit gonadotropin-induced activation of mitogen-activated protein kinase 3/1 in pig cumulus-oocyte complex", Reproductive Biology and Endocrinology, Jan. 7, 2015, pp. 1-12.
Conti et al., "Novel signaling mechanisms in the ovary during oocyte maturation and ovulation", Molecular and Cellular Endocrinology, vol. 356, No. 1-2, Jun. 1, 2012, pp. 65-73.
Conti et al., "Role of cyclic nueleotide phosphodiesterases in resumption of meiosis", Molecular and Cellular Endocrinology, 145, 1998, pp. 9-14.
Conti et al., "Role of cyclic nucleotide signaling in oocyte maturation", Molecular and Cellular Endocrinology, 187, 2002, pp. 153-159.
Hiradate et al., "C-type natriuretic peptide inhibits porcine oocyte meiotic resumption", Zygote 22, Aug. 2013, Cambridge University Press, pp. 372-377.
Sato et al., "C-Type Natriuretic Peptide Stimulates Ovarian Follicle Development", Mol Endocrinol, Jul. 2012, 26(7), pp. 1158-1166.
Shu et al, "Effects of cilostamide and forskolin on the meiotic resumption and embryonic development of immature human oocytes", Human Reproduction, vol. 23, No. 3, 2008, pp. 504-513.
De Vos et al., "Clinical outcome of non-hCG-primed oocyte in vitro maturation treatment in patients with polycystic ovaries and polycystic ovary syndrome", Fertility and Sterility, vol. 96, No. 4, Oct. 2011, pp. 860-864.e1.
Franciosi et al., "Natriuretic Peptide Precursor C Delays Meiotic Resumption and Sustains Gap Junction-Mediated Communication in Bovine Cumulus-Enclosed Oocytes", Biology of Reproduction, 2014, 91(3):61, pp. 1-9.
Guzman et al., "Developmental capacity of in vitro-matured human oocytes retrieved from polycystic ovary syndrome ovaries containing no follicles larger than 6mm", Reproductive Endocrinology, vol. 98, No. 2, Aug. 2012, pp. 503-507.e2.
Nogueira et al., "Effect of Phosphodiesterase Type 3 Inhibitor on Developmental Competence of Immature Mouse Oocytes In Vitro", Biology of Reproduction 69, Aug. 2003, pp. 2045-2052.
Santiquet et al., "New Elements in the C-Type Natriuretic Peptide Signaling Pathway Inhibiting Swine In Vitro Oocyte Meiotic Resumption", Biology of Reproduction, New York, NY, vol. 91, No. 1, Jun. 2014, pp. 1-8.
Thomas et al., "Bovine Cumulus Cell-Oocyte Gap Junctional Communication During In Vitro Maturation in Response to Manipulation of Cell-Specific Cyclic Adenosine 3',5'-Monophosophate Levels", Biology of Reproduction 70, 2004, pp. 548-556.
Tsafriri et al., "Oocyte Maturation Involves Compartmentalization and Opposing Change of cAMP Levels in Follicular Somatic and Germ Cells: Studies Using Selective Phosphodiesterase Inhibitors", Developmental Biology 178, 1996, Article No. 0226, Academic Press, Inc., pp. 393-402.

(Continued)

*Primary Examiner* — Padmashri Ponnaluri
(74) *Attorney, Agent, or Firm* — Dinsmore & Shohl LLP

(57) ABSTRACT

The present invention relates to a composition and method for assisted reproductive technology in mammals. In particular, the present invention provides compositions and methods for in vivo maturation of an immature cumulus oocyte complex (COC), thereby enhancing the embryology outcome.

15 Claims, 10 Drawing Sheets

(56) References Cited

OTHER PUBLICATIONS

Vanhoutte et al., "Prematuration of human denuded oocytes in a three-dimensional co-culture system: effects on meiosis progression and developmental competence", Human Reproduction, vol. 24, No. 3, 2009, pp. 658-669.

Zhang et al., "Brain Natriuretic Peptide and C-Type Natriuretic Peptide Maintain Porcine Oocyte Meiotic Arrest", J. Cellular Physiology, 230, 2015, pp. 71-81.

Zhang et al., "Estradiol Promotes and Maintains Cumulus Cell Expression of Natriuretic Peptide Receptor 2 (NPR2) and Meiotic Arrest in Mouse Oocytes In Vitro", Endocrinology, vol. 152, No. 11, Nov. 2, 2011, pp. 4377-4385.

Zhang et al., "Granulosa Cell Ligand NPPC and Its Receptor NPR2 Maintain Meiotic Arrest in Mouse Oocytes", Science, Oct. 15, 2010, pp. 366-369, www.sciencemag.org.

Extended European Search Report pertaining to European Application No. EP14199324 filed Dec. 19, 2014, completed Feb. 12, 2015.

International Search Report pertaining to PCT/BE2015000068 filed Dec. 21, 2015, completed May 30, 2016.

Thomas et al., "Effect of Specific Phosphodiesterase Isoenzyme Inhibitors During In Vitro Maturation of Bovine Oocytes on Meiotic and Developmental Capacity", Biology of Reproduction 71, 2004, pp. 1142-1149.

* cited by examiner

A

B

IN VITRO MATURATION OF A MAMMALIAN CUMULUS OOCYTE COMPLEX

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention in general relates to compositions and methods for assisted reproductive technology in mammals. Specifically, the invention relates to compositions and methods for in vitro maturation of a mammalian cumulus oocyte complex.

BACKGROUND TO THE INVENTION

In human infertility practice, the classical in vitro fertilization (IVF) or intracytoplasmic sperm injection (ICSI) technologies are still used after superovulation with expensive hormone therapies to obtain large follicles (i.e at least 17 mm diameter). Both the costs of the hormones, their associated risk for acute and long term complications and the inconvenience of repeated hospital visits to monitor follicle growth incite the development of a less costly and better tolerated therapeutic procedure for infertile couples with a normal/high follicular reserve.

Oocyte in vitro maturation (IVM) is a technique that enables to mature germinal vesicle (GV)—stage oocytes that are enclosed in a firmly condensed corona cumulus layer (cumulus oocyte complexes (COCs)). These oocytes can be obtained by ultrasound-guided needle puncture before ovulation has been triggered by administration of human chorionic gonadotrophin (hCG) or early after hCG administration. Therefore, oocyte IVM has the potential to simplify fertility treatment or to reduce risks and costs related to hormone (hCG) stimulation in patients with normal or high ovarian follicular reserve. This follicular reserve is routinely determined by measurement of the anti-müllerian hormone levels and by ultrasound-guided follicle count on day 3 of the menstrual cycle.

For oocyte IVM, using ultrasound-guided needle puncture, the oocytes can be collected from small (<10 mm) follicles, in minimally stimulated or unstimulated ovaries and matured in vitro. However, interfering with the normal development of the oocyte at an early stage of development (e.g. when the follicle has only attained a diameter of 10 mm or less) not only produces fewer matured oocytes, but also decreases subsequent embryo development and implantation. In particular, successful implantation rate per embryo following IVM is usually less than 10% and is only half as successful as the rate that is reported for a routine IVF or ICSI procedure. The rate of early pregnancy loss seems to be variable, but is generally greater than after IVF/ICSI. For human patients, the reduced meiotic maturation rate (50%) currently forms a major bottleneck of current IVM technologies, together with the observed deficiency in embryo development of the matured oocytes (De Vos et at, Fertil. Steril. 2011; 96(4) 860-864; Guzman et al, Fertil. Steril. 2012; 98(2): 503-507). Therefore, the reduced developmental potential and implantation rate of IVM embryos needs to be addressed before the method can become widely accepted.

The cornerstone of the IVM culture is the provision of an appropriate environment for the attainment of developmental competence. This requires mainly hormonal intervention and the activation of necessary signaling pathways by using chemical compounds that allow synchronization of nuclear and cytoplasmic maturation processes within the oocyte. The rationale of a prolonged oocyte maturation period in vitro is to promote a longer interaction between the immature oocyte with adequately conditioned cumulus cells.

The signaling pathways between follicular cells and oocytes responsible for meiotic arrest have been extensively investigated. Meiotic arrest is maintained by production of high levels of cyclic adenosine monophosphate (cAMP). Intra-oocyte cAMP concentration is regulated by the activity of phosphodiesterase (PDE) enzymes that degrade cAMP. Recent studies showed that cGMP is produced in the cumulus cells upon activation of the guanilyl-cyclase coupled natriuretic peptide receptor type-2 (NPR2). NPR2 activity is induced by its ligand natriuretic peptide precursor C (NPPC), which is mainly synthesized by mural granulosa cells and cleaved into the C-type natriuretic peptide (CNP). cGMP is then transferred to the oocyte where it [Inhibits] *inhibits* the hydrolysis of cAMP by the phosphodiesterase PDE3A. This inhibition maintains a high concentration of cAMP and thus blocks meiotic progression. (Tsafriri et al., Dev. Biol. 1996, 178(2): 393-402; Conti et al., Mol. Cell. Endocrinol. 1998, 145(1-2): 9-14; Conti et al., Mol. Cell. Endocrinol. 2002, 187(1-2): 153-159).

Pharmacological interference with the cAMP levels in the in vitro matured oocyte, derived from different species such as mouse, bovine, human, has been previously attempted in order to promote oocyte meiotic arrest, and allow for the acquisition of oocyte competence (Nogueira et al. Biol. Reprod. 2003, 69(6): 2045-2052; Thomas et al. Biol. Reprod. 2004, 71(4): 1142-1149; Shu et al. Hum. Reprod. 2008, 23(3): 504-513; Vanhoutte et al., Hum. Reprod. 2009, 24(3); 658-669). Nevertheless, no major improvements have been reported at the level of embryonic developmental potential.

Recently, the CNP/NPR2 signaling pathway has shown to be a crucial regulatory mechanism in the maintenance of oocyte meiotic arrest in mid-size and fully-grown follicles (Zhang et al. J. Cell, Physiol. 2015, 230(1): 71-81; Sato et al. Mol. Endocrinol. 2012, 26: 1158-1166, Franciosi et al. Biol. Reprod. 2014, 91(3): 61, Santiquet et al. Biol. Reprod. 2014, 91(1): 16). However, the major problem in the above-mentioned studies is that the COCs can only be kept for a short time in meiotic arrest, and hence, in vitro maturation of only mid-size to large follicles was successful and maturation of small early antral follicles failed. Therefore, it is currently a major challenge to delay the start of meiotic resumption of small early antral follicles as well in order to improve their IVM process. In particular, such a protocol should not affect the further in vitro maturation. This challenge is even higher for such small early antral follicles as they need to gain or retain the capability of completing the nuclear maturation (i.e. moving from non-surrounded nucleolus (NSN) into surrounded nucleolus (SN) stage) before moving into the next steps of potential development, or even keeping the interconnection between oocytes and cumulus, allowing for the transfer of the nutrients from cumulus (e.g. RNA cargo)).

SUMMARY OF THE INVENTION

The present invention is directed to compositions and methods for assisted reproductive technology in mammals.

In particular, the present invention provides compositions and methods for in vitro maturation of an immature cumulus oocyte complex (COC), thereby enhancing the embryology outcome.

In the context of the present invention, the immature mammalian COC is collected without prior hCG stimulation or after hCG stimulation. In a preferred embodiment, any triggers, including high doses of FSH, LHRH and its agonists, recombinant LH or LH analogs are avoided prior to collection of COCs in vitro.

In a first aspect, the present invention provides a capacitation medium for in vitro maturation of a mammalian cumulus oocyte complex (COC), said medium comprising 0.1 to 50 nM C-type natriuretic peptide (CNP), estradiol and FSH. In a particular embodiment, the capacitation medium comprises 10 to 25 nM CNP, even more in particular 25 nM CNP.

In a specific embodiment, the capacitation medium comprises 1 to 1000 nM estradiol, most preferably 10 nM estradiol. In another embodiment, the capacitation medium comprises 0.1 to 10 [mIU/ml] *mIU/ml* of FSH, in particular 1 to 5 [mIU/ml] *mIU/ml* FSH, even more in particular 2.5 [mIU/ml] *mIU/ml* FSH or 1 *mIU/ml* FSH. In a further embodiment, the capacitation medium comprises 25 nM CNP, 10 nM estradiol and 2.5 or 1 [mIU/ml] *mIU/ml* FSH. In yet another aspect, the capacitation medium comprises equipotent doses of recombinant FSH, FSH analogs, or FSH mimetic molecules.

In yet another embodiment, the capacitation medium comprises 0.1-10 ng/ml insulin, in particular 5 ng/ml insulin. In another aspect, the capacitation medium comprises equipotent doses of insulin analogs or insulin mimetic molecules.

In a further embodiment, the capacitation medium comprises an oocyte-secreted factor. The oocyte-secreted factors as used herein are selected from the group consisting of GDF-9, BMP-15, FGF-8 or any combination thereof; in particular at concentrations in the capacitation medium ranging from 10-100 ng/ml each respectively. In a particular embodiment, the oocyte-secreted factors are recombinant proteins. In yet another aspect, the oocyte-secreted factors are heterodimeric proteins.

In yet another further embodiment, the capacitation medium comprises 0.1 to 50 nM CNP, most preferably 25 nM CNP; 1 to 1000 nM estradiol, most preferably 10 nM estradiol; 0.1 to 10 *mIU/ml* FSH, most preferably 2.5 [milling] *mIU/ml* FSH or 1 [mIU/ml] *mIU/ml* FSH; 0.1 to 10 ng/ml insulin, most preferably 5 ng/ml insulin; and an oocyte-secreted factor selected from the group consisting of GDF-9, BMP-15, FGF-8 or any equivalent or combination thereof.

The invention also provides an in vitro method for maturation of immature mammalian COCs.

In a first aspect, the method comprises collecting an immature COC in collection medium, contacting the mammalian COC with a capacitation medium that comprises 0.1 to 50 nM CNP, estradiol and FSH, and further contacting the mammalian COC with a maturation medium. In said method, the immature COC is typically contacted with the collection medium for minimally 30 minutes to maximally 2 hours. Also in said method, and after contacting with the collection medium, the mammalian COC is contacted with the capacitation medium that maintains meiotic arrest. In particular, the COC is contacted with the capacitation medium for a time sufficient to reach an advanced stage of development as evidenced for example by reorganization of oocyte's chromatin into a condensed stage or the so-called surrounded nucleolus (SN) configuration, observed at the GV-stage. After this period, oocytes will be capable to undergo germinal vesicle breakdown (GVBD) following a stimulus for meiotic resumption. Even more in particular, the mammalian COC is contacted with the capacitation medium for minimum 2 h and maximum 96 h. In a further particular embodiment, the mammalian COC is contacted with the capacitation medium for a period determined by the size of the follicle. More in particular, follicle size is determined at the moment of COC retrieval, such as for example by ultrasound imaging. Follicles with a diameter of 1 to 5 mm are preferred to stay for at least 48 h in the capacitation medium. For follicles with a diameter of >5 to 10 mm the COCs are preferred to stay for at least 24 h in the capacitation medium, and follicles with a diameter of more than 10 mm are preferred to stay for at least 2 h in the capacitation medium. In another embodiment, the mammalian COC is contacted with a maturation medium to allow further meiotic maturation of the oocyte.

In a specific embodiment, in the in vitro method according to the present invention, the capacitation medium comprises 1-1000 nM estradiol, more in particular 10 nM estradiol. In another embodiment, in the in vitro method according to the present invention, the capacitation medium comprises 0.1- to 10 [mIU/ml] *mIU/ml* FSH, more in particular 2.5 [mIU/ml] *mIU/ml* FSH or 1 [mIU/ml] *mIU/ml* FSH. In yet another aspect, the capacitation medium comprises equipotent doses of recombinant FSH, FSH analogs, or FSH mimetic molecules.

In yet another embodiment, in the in vitro method according to the present invention, the capacitation medium comprises 0.1 to 10 ng/ml insulin, more in particular 5 ng/ml insulin. In another aspect, the capacitation medium comprises equipotent doses of insulin analogs or insulin mimetic molecules.

In a further embodiment, in the in vitro method according to the present invention, the capacitation medium comprises an oocyte-secreted factor. The oocyte-secreted factors as used herein are selected from the group consisting of GDF-9, BMP-15, FGF-8 or any combination thereof; in particular at concentrations in the capacitation medium ranging from 10-100 ng/ml each respectively. In a particular embodiment, the oocyte-secreted factors are recombinant proteins. In yet another embodiment, the oocyte-secreted factors are heterodimeric proteins.

In another embodiment, in the in vitro method according to the present invention, the mammalian COC is contacted with the capacitation medium for a period of minimal 2 h to maximum 96 h. This time is sufficient to reach an advanced stage of development, as evidenced for example by reorganization of oocyte's chromatin into a condensed stage or the so-called surrounded nucleolus (SN) configuration. In a further particular embodiment, the mammalian COC is contacted with the capacitation medium for a period determined by the size of the follicle. More in particular, follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least 2 h in the capacitation medium. The capacitation period enables the oocyte to gain competence to resume meiosis, which is only evaluated after the meiotic stimulus is triggered. In another embodiment, the mammalian COC is contacted with a maturation medium (meiotic stimulus) to allow further meiotic maturation of the oocyte, which is evidenced under the inverted microscope by the breakdown of the germinal vesicle (GVBD) and extrusion of the first polar body (PB).

In a particular embodiment, in the in vitro method according to the present invention, the mammalian COC is contacted with the capacitation medium in a non-adherent or adherent culture plate, in particular in a non-adherent culture plate.

In a further embodiment, in the in vitro method according to the present invention, the immature COC is contacted with the collection medium for minimally 30 minutes to maximally 2 hours.

In another embodiment, the in vitro method according to the present invention is part of an assisted reproduction technology. In a particular embodiment, said assisted reproduction technology comprises in vitro fertilization or ICSI.

In a particular embodiment of the invention, the mammalian COC is a human COC.

In a further aspect, the present invention provides a kit for in vitro maturation of an immature mammalian COC. Said kit comprises a capacitation medium as described herein. In a particular embodiment, in a kit according to the present invention, the capacitation medium comprises 0.1 to 50 nM CNP, estradiol and FSH. In a more particular embodiment, in a kit according to the present invention, the capacitation medium comprises 10 to 25 nM CNP, preferably 25 nM CNP. In a specific embodiment, the capacitation medium in the kit comprises 1-1000 nM estradiol, preferably 10 nM estradiol. In another embodiment, the capacitation medium in the kit comprises 0.1 to 10 [mIU/ml] *mIU/ml* FSH, more in particular 2.5 [mIU/ml] *mIU/ml* FSH or 1 [mIU/ml] *mIU/ml* FSH. In yet another aspect, the capacitation medium comprises equipotent doses of recombinant FSH, FSH analogs, or FSH mimetic molecules. In yet another embodiment, in the kit according to the present invention, the capacitation medium comprises 0.1 to 10 ng/ml insulin, more in particular 5 ng/ml insulin. In another aspect, the capacitation medium comprises equipotent doses of insulin analogs or insulin mimetic molecules. In another embodiment, in the kit according to the present invention, the capacitation medium comprises 0.1 to 50 nM CNP, preferably 25 nM CNP; 1 to 1000 nM estradiol, preferably 10 nM estradiol; 0.1 to 10 [mIU/ml] *mIU/ml* FSH, preferably 2.5 [mIU/ml] *mIU/ml* FSH or 1 [mIU/ml] *mIU/ml* FSH; and 0.1 to 10 ng/ml insulin, preferably 5 ng/ml insulin.

In a further embodiment, in a kit according to the present invention, the capacitation medium comprises an oocyte-secreted factor. The oocyte-secreted factors used herein are selected from the group consisting of GDF-9, BMP-15, FGF-8 or any combination thereof. In particular at concentrations in the capacitation medium ranging from 10-100 ng/ml each respectively. In a particular embodiment, the oocyte-secreted factors used herein are recombinant proteins or heterodimeric proteins.

In another embodiment, the kit for in vitro maturation of an immature mammalian COC comprises (a) a collection medium comprising natural or man-made chemical compounds inhibiting naturally occurring phosphodiesterases or natural inhibitors of oocyte meiosis; (b) a capacitation medium as described herein; (c) a maturation medium; (d) adherent and/or non-adherent culture plates; and (e) instructions for use of the kit.

In another aspect, the present invention provides the use of a capacitation medium for in vitro maturation of an immature mammalian COC. Said capacitation medium comprises 0.1 to 50 nM CNP, estradiol and FSH, as described herein. In a specific embodiment, said capacitation medium comprises 1 to 1000 nM estradiol. In another embodiment, the capacitation medium comprises [0.1to 10 mIU/ml] *0.1 to 10 mIU/ml* of FSH, preferably 2.5 [mIU/ml] *mIU/ml* FSH or 1 [mIU/ml] *mIU/ml* FSH. In yet another aspect, the capacitation medium comprises equipotent doses of recombinant FSH, FSH analogs, or FSH mimetic molecules. In yet another embodiment, the capacitation medium comprises 0.1-10 ng/ml insulin, preferably 5 ng/ml insulin. In another aspect, the capacitation medium comprises equipotent doses of insulin analogs or insulin mimetic molecules. In a further embodiment, in the use of the capacitation medium according to the present invention, the capacitation medium comprises an oocyte-secreted factor. The oocyte-secreted factors as used herein are selected from the group consisting of GDF-9, BMP-15, FGF-8 or any combination thereof. In a particular embodiment, the oocyte-secreted factors are recombinant proteins. In yet another aspect, the oocyte-secreted factors are heterodimeric proteins.

In a particular embodiment, in the use of the capacitation medium according to the present invention, the mammalian COC is contacted with the capacitation medium for a period of minimum 2 h to maximum 96 h. More in particular, in the use of the capacitation medium, the mammalian COC is contacted with the capacitation medium to maintain oocytes under meiotic arrest and to allow acquisition of cytoplasmic maturation. In particular, the COC is contacted with the capacitation medium for a time sufficient to reach an advanced stage of development, as evidenced for example by reorganization of oocyte's chromatin into a condensed stage or the so-called surrounded nucleolus (SN) configuration. In a further particular embodiment, the mammalian COC is contacted with the capacitation medium for a period determined by the size of the follicle. More in particular, follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least 2 h in the capacitation medium. Assessment of oocyte maturation at the nuclear level i.e. chromatin remodeling within the oocyte, is assessed under a fluorescent microscope.

In a particular embodiment, in the use of the capacitation medium according to the present invention, the mammalian COC is contacted with the capacitation medium in a non-adherent or adherent culture plate, in particular a non-adherent culture plate.

In another embodiment, the use of the capacitation medium maintains the oocyte of a mammalian COC in meiotic arrest. Based on the ability to maintain the oocytes in meiotic arrest without affecting their further maturation, the use of the capacitation medium of the instant invention creates a flexible IVMI method when compared to the currently used IVM methods. Due to the possible flexibility in the extension of in-vitro culture i.e. the capacitation interval- all important technical work (like micro injecting the oocytes) can now fall within the normal working hours. Evidently, this is an important practical improvement over the current IVM protocols.

In a further embodiment, the use of the capacitation medium according to the present invention is part of an assisted reproduction technology. In a particular embodiment, said assisted reproduction technology comprises in vitro fertilization or ICSI.

Further applications based on the use of the capacitation medium of the present invention reside in the increased IVM performance of COCs obtained from smaller follicles than normally used.

By being able to mature smaller follicles, one;

has the possibility to cryopreserve developmentally competent matured oocytes from small antral follicles;

has the possibility to culture COC from small antral follicles (important for the field of Fertility preservation in case of Cancer treatment) where the COC will be obtained from dissection of smaller follicles than those punctured by Ultrasound guided trans-vaginal retrieval.

Another aspect of the present invention is based on the use of a kit comprising a capacitation medium for in vitro maturation of a mammalian COC. Said kit comprises a capacitation medium as described herein. In a particular embodiment, in a kit according to the present invention, the capacitation medium comprises 0.1 to 50 nM CNP, estradiol and FSH. In a specific embodiment, the capacitation medium in the kit comprises 1-1000 nM estradiol. In another embodiment, the capacitation medium in the kit comprises 0.1 to 10 [mIU/ml] *mIU/ml* FSH. In yet another embodiment, in the kit according to the present invention, the capacitation medium comprises 0.1 to 10 ng/ml insulin. In another embodiment, in the kit according to the present invention, the capacitation medium comprises 0.1 to 50 nM CNP, preferably 25 nM CNP; 1 to 1000 nM estradiol, preferably 10 nM estradiol; and 0.1 to 10 [mIU/ml] *mIU/ml* FSH, preferably 2.5 [mIU/ml] *mIU/ml* FSH or 1 [mIU/ml] *mIU/ml* FSH. In yet another aspect, the capacitation medium comprises equipotent doses of recombinant FSH, FSH analogs, or FSH mimetic molecules.

In yet another embodiment, in the kit according to the present invention, the capacitation medium comprises 0.1 to 10 ng/ml insulin, more in particular 5 ng/ml insulin. In another aspect, the capacitation medium comprises equipotent doses of insulin analogs or insulin mimetic molecules.

In a further embodiment, in a kit according to the present invention, the capacitation medium comprises an oocyte-secreted factor. The oocyte-secreted factors used herein are selected from the group consisting of GDF-9, BMP-15, FGF-8 or any combination thereof. In a particular embodiment, the oocyte-secreted factors used herein are recombinant proteins or heterodimeric proteins.

In another embodiment, the use of a kit comprising a capacitation medium for in vitro maturation of an immature mammalian COC comprises contacting the mammalian COC with the capacitation medium for a period of minimum 2 h to maximum 96 h. More in particular, in the use of a kit comprising a capacitation medium, the mammalian COC is contacted with the capacitation medium to induce meiotic arrest and to allow maturation. In particular, the COC is contacted with the capacitation medium for a time sufficient to reach an advanced stage of development, as evidenced for example by reorganization of oocyte's chromatin into a condensed stage or the so-called surrounded nucleolus (SN) configuration. In a further particular embodiment, the mammalian COC is contacted with the capacitation medium for a period determined by the size of the follicle. More in particular, follicle size is determined at the moment of COC retrieval by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least 2 h in the capacitation medium.

Assessment of oocyte maturation at the nuclear level i.e. chromatin remodeling within the oocyte, is assessed under a fluorescent microscope.

Another aspect of the present invention is based on the use of a kit comprising (a) a collection medium comprising natural or man-made chemical compounds inhibiting naturally occurring phosphodiesterases or natural inhibitors of oocyte meiosis; (b) a capacitation medium as described herein; (c) a maturation medium; (d) adherent and/or non-adherent culture plates; and (e) instructions for use of the kit.

In a particular aspect of the present invention, the use of a kit for in vitro maturation of an immature mammalian COC comprises contact of the COC with the collection medium for minimally 30 minutes to maximum 2 hours. In another aspect, in the use of a kit according to the present invention, the mammalian COC is contacted with the capacitation medium for a period of minimum 2 h to maximum 96 h. More in particular, in the use of a kit comprising a collection medium, a capacitation medium, a maturation medium, adherent and/or non-adherent culture plates and instructions for use, the mammalian COC is contacted with the capacitation medium to induce meiotic arrest and to allow maturation. In particular, the COC is contacted with the capacitation medium for a time sufficient to reach an advanced stage of development, as evidenced for example by reorganization of oocyte's chromatin into a condensed stage or the so-called surrounded nucleolus (SN) configuration. In a further particular embodiment, the mammalian COC is contacted with the capacitation medium for a period determined by the size of the follicle. More in particular, follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least 2 h in the capacitation medium.

The capacitation period enables the oocyte to gain competence to resume meiosis, which is only evaluated after the meiotic stimulus is triggered. In another embodiment, the mammalian COC is contacted with a maturation medium (meiotic stimulus) to allow further meiotic maturation of the oocyte, which is evidenced under the Inverted microscope by the breakdown of the germinal vesicle (GVBD) and extrusion of the first polar body (PB).

In a particular embodiment, in the use of a kit according to the present invention, the mammalian COC is contacted with the capacitation medium in a non-adherent or adherent culture plate.

In another embodiment, in the use of a kit according to the present invention, the capacitation medium maintains the oocyte of a mammalian COC in meiotic arrest.

In a further embodiment, the use of a kit according to the present invention induces maturation of a mammalian COC.

In yet another embodiment, the use of kit according to the present invention is part of an assisted reproduction technology. In a particular embodiment, said assisted reproduction technology comprises in vitro fertilization or iCSI.

Numbered Embodiments of the Present Invention are as Follows:

1. A capacitation medium for in vitro maturation of an immature mammalian cumulus oocyte complex, the medium comprising 0.1-50 nM C-type natriuretic peptide (CNP), estradiol and Follicle Stimulating Hormone (FSH); in particular comprising 10-50 nM of C-type natriuretic peptide (CNP).; more in particular 25 nM of CNP.

2. The capacitation medium according to claim 1 wherein said medium comprises 1-1000 nM estradiol.

3. The capacitation medium according to claim 1, wherein said medium comprises 0.1 to 10 [mIU/ml] *mIU/ml* of Follicle Stimulating Hormone (FSH).

4. The capacitation medium according to any one of preceding claims, wherein said medium also comprises 0.1-10 ng/ml insulin.

5. The capacitation medium according to any one of preceding claims, wherein said medium comprises an oocyte-secreted factor.

6. The capacitation medium according to claim 5, wherein the oocyte-secreted factor is selected from the group consisting of GDF-9, BMP-15, FGF-8, their analogues or any combination thereof; in particular at concentrations in the capacitation medium ranging from 10-100 ng/ml for each of said factors respectively.

7. An in vitro method for maturation of an immature mammalian cumulus oocyte complex, the method comprising collecting an immature cumulus oocyte complex in collection medium, contacting the mammalian cumulus oocyte complex with a capacitation medium that comprises 0.1-50 nM CNP (in particular 10-50 nM CNP), estradiol and FSH, and further contacting the mammalian cumulus oocyte complexes with a maturation medium.

8. The method according to claim 7, wherein the capacitation medium comprises 1-1000 nM estradiol.

9. The method according to claim 7, wherein the capacitation medium comprises 0.1-10 *mIU/ml* FSH.

10. The method according to any one of claims 7 to 9, wherein the capacitation medium also comprises 0.1-10 ng/ml insulin.

11. The method according to any one of claims 7 to 10, wherein the capacitation medium comprises an oocyte-secreted factor.

12. The method according to claim 11, wherein the oocyte-secreted factor is selected from the group consisting of GDF-9, BMP-15, FGF-8, their analogues, or any combination thereof; in particular at concentrations in the capacitation medium ranging from 10-100 ng/ml for each of said factors respectively.

13. The method according to any one of claims 7 to 12, wherein the mammalian cumulus oocyte complex is a human cumulus oocyte complex.

14. The method according to any one of claims 7 to 13, wherein the mammalian cumulus oocyte complex is contacted with the capacitation medium for a period of minimum 2 h to maximum 96 h.

15. The method according to any one of claims 7 to 14, wherein the mammalian cumulus oocyte complex is contacted with the capacitation medium in a non-adherent or adherent culture plate; in particular a non-adherent culture plate.

16. The method according to claim 7, wherein the immature cumulus oocyte complex is contacted with the collection medium for minimally 30 minutes to maximally 2 hours.

17. The method according to any one claims 7 to 16, wherein the method is part of an assisted reproduction technology.

18. The method according to claim 17, wherein the assisted reproduction technology comprises in vitro fertilization or ICSI or fertility preservation.

19. A kit for in vitro maturation of an immature mammalian cumulus oocyte complex, the kit comprising a capacitation medium according to any one of claims 1 to 6.

20. A kit for in vitro maturation of an immature mammalian cumulus oocyte complex, the kit comprising:

(a) a collection medium comprising natural or man-made chemical compounds inhibiting naturally occurring phosphodiesterases or natural inhibitors of oocyte meiosis;

(b) a capacitation medium according to any one of claims 1 to 6;

(c) a maturation medium;

(d) non-adherent and/or adherent culture plates; and (e) instructions for use of the kit 21. Use of a capacitation medium according to any one of claims 1 to 6 for in vitro maturation of a mammalian cumulus oocyte complex.

22. Use of a capacitation medium according to any one of claims 1 to 6 wherein the mammalian cumulus oocyte complex is contacted with the capacitation medium for a period of minimum 2 h to maximum 96 h.

23. Use of a capacitation medium according to any one of claims 1 to 6 wherein the mammalian cumulus oocyte complex is contacted with the capacitation medium in a non-adherent or adherent culture plate; in particular with a non-adherent culture plate.

24. Use of a capacitation medium according to any one of claims 1 to 6 to maintain the oocyte of a mammalian cumulus oocyte complex in meiotic arrest.

25. Use of a capacitation medium according to any one of claims 1 to 6 as part of an assisted reproduction technology.

26. Use of a capacitation medium according to claim 25 wherein the assisted reproduction technology comprises in vitro fertilization or ICSI.

27. Use of a capacitation medium according to any of claims 1 to 6 in fertility preservation methods, such as for example in case of Cancer treatment or in case of oocyte banking (the latter in particular for Age Bankers (35-40 years)).

28. Use according to claim 27, wherein the fertility preservation method includes the cryopreservation from small antral follicles.

29. Use according to claim 28, wherein the capacitation medium is used for the in vitro maturation of said cryopreserved small antral follicles.

30. Use of a capacitation medium according to any of claims 1 to 6 in fertility preservation in case of cancer treatment.

31. Use of a capacitation medium according to any of claims 1 to 6 in fertility preservation in case of oocyte banking.

32. Use of a kit according to claims 19 or 20 for in vitro maturation of mammalian cumulus oocyte complexes.

33. Use of a kit according to claim 20, wherein the immature cumulus oocyte complex is contacted with the collection medium for minimally 30 minutes to maximally 2 hours.

34. Use of a kit according to claim 19 or 20 wherein the mammalian cumulus oocyte complex is contacted with the capacitation medium for a period of minimum 2 h to maximum 96 h.

35. Use of a kit according to claim 19 or 20, wherein the mammalian cumulus oocyte complex is contacted with the capacitation medium in a non-adherent or adherent culture plate; in particular with a non-adherent culture plate.

36. Use of a kit according to claim 19 or 20 to maintain the oocyte of a mammalian cumulus oocyte complex in meiotic arrest.

37. Use of a kit according to claim 19 or 20 to induce maturation of a mammalian cumulus oocyte complex.

38. Use of a kit according to claim 19 or 20 as part of an assisted reproduction technology.

39. Use of a kit according to claim 38 wherein the assisted reproduction technology comprises in vitro fertilization or ICSI.

40. Use of a kit according to claim 19 or 20 as part of a fertility preservation method; in particular fertility preservation in case of cancer treatment.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

Figure 1:
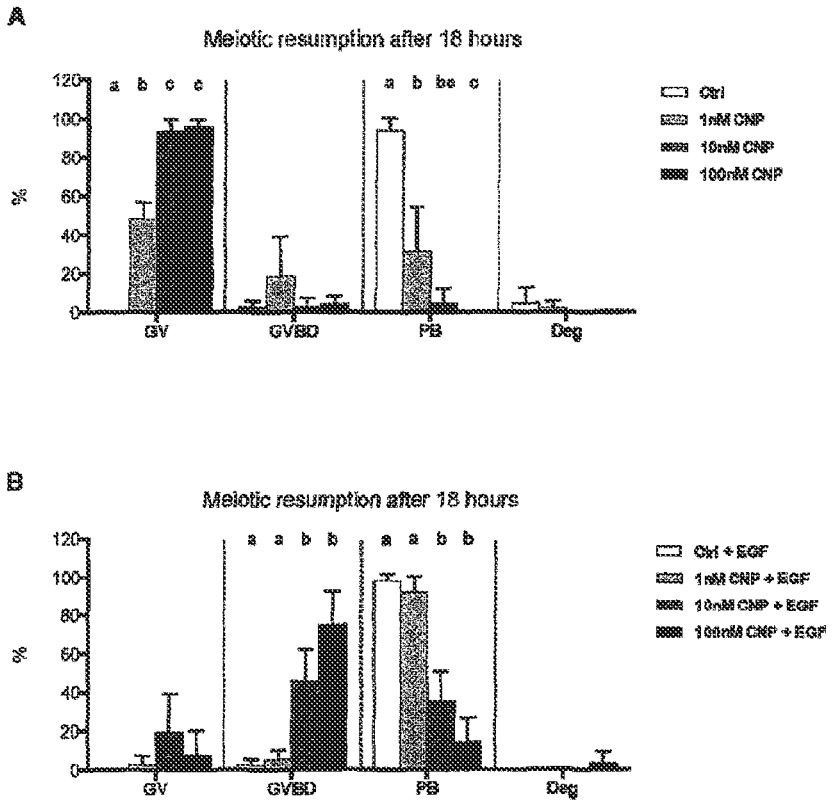
FIG. 1: Dose dependent effect of CNP-22 on the progression of meiotic maturation Pre-ovulatory COCs were in vitro matured for 18 hours in presence of 0 (Control), 1, 10, 100 nM CNP-22 (A) and in combination with 4 ng/mL EGF (B). After maturation period, oocyte nuclear maturation was assessed. Each bar represents mean±SD of experimental data obtained from three replicates (at least 33 oocytes/treatment). Different letters indicate significant differences (P<0.05).

Following a Pre-IVM period of 48 hours and an IVM period of 18 hours, oocytes were in vitro fertilized and embryos cultured for up to 5 days. Evaluation parameters were 2-cell rate (fertilization) (A), and blastocyst formation on day 5 (D5 Blast/2-cell) (B). Each bar in (A) & (B) represents experimental data obtained from four replicates (at least 64 oocytes/treatment); results are shown as the mean±SD.

(C) The 2-cell rate and Blastocyst rate on day 5 (D5 Blast/2-cell) for two reference controls is shown. immature COCs were obtained from small antral follicles of 20 days-old mice and in vitro matured for 18 hours in presence of 100 ng/mL EREG [20do (IVM)]. Similarly, gold standard, in vivo grown oocytes (controls) were obtained from mice aged 26-27 days, following 48 hrs of eCG priming followed by 14 hrs hCG. The data for these controls come from 2 replicates (at least 56 oocytes/treatment) (P<0.05).

Figure 6:
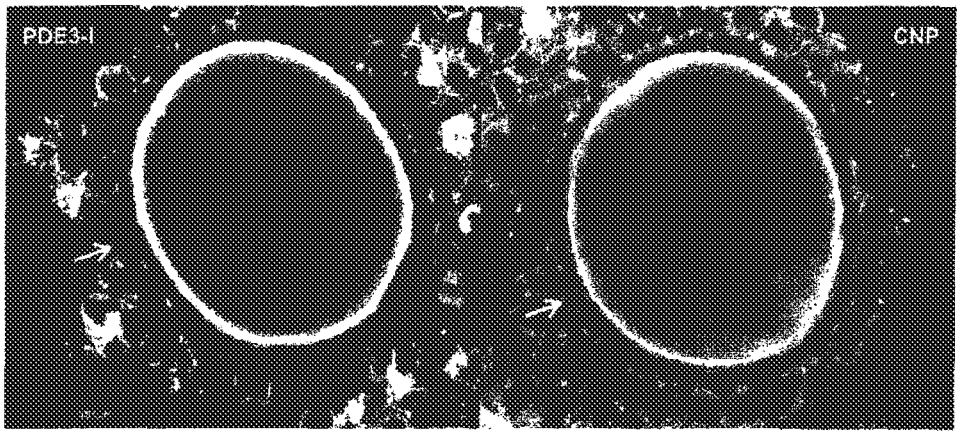

FIG. 6: Effect of CNP on In vitro cultured cumulus-oocyte connections

Transzonal projections (TZP) in mouse COCs following 48 h of culture in presence of either a PDE3-Inhibitor or CNP. Left in the presence of a PDE3-inhibitor, right in the presence of CNP. The zona pellucida surrounding the oocyte is delineated and indicated with an arrow. In the presence of a PDE3-inhibitor, the zone pellucida is black indicating hardly any transzonal projections. Beyond any expectation, in the presence of CNP, the zona pellucida is full with transzonal projections indication of a sound cumulus-oocyte connection.

Figure 7:
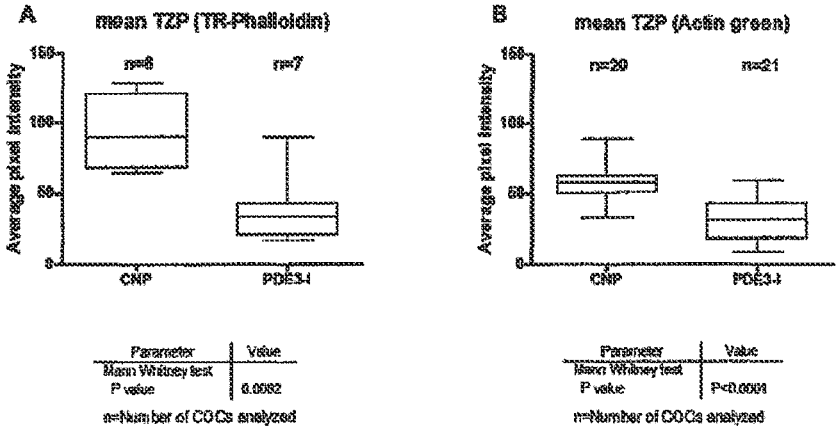

FIG. 7: Actin Filament staining in zona pellucida of in vitro cultured cumulus-oocyte connections Average pixel intensity on the zona pellucida in COCs exposed to CNP or a PDE3 inhibitor. In (A), Org9935 was used as inhibitor for PDE3 and actin filaments were evidenced with Texas-red bound phalloidin; while in (B), Cilostamide was used as inhibitor far PDE3 and actin filaments were evidenced with Actin green™. (n=number of COCs analysed). The CNP and PDE3i groups were statistically compared using a Mann Whitney test with a P value for panel A of 0.0082 and a P value for panel B<0.0001.

Figure 8:
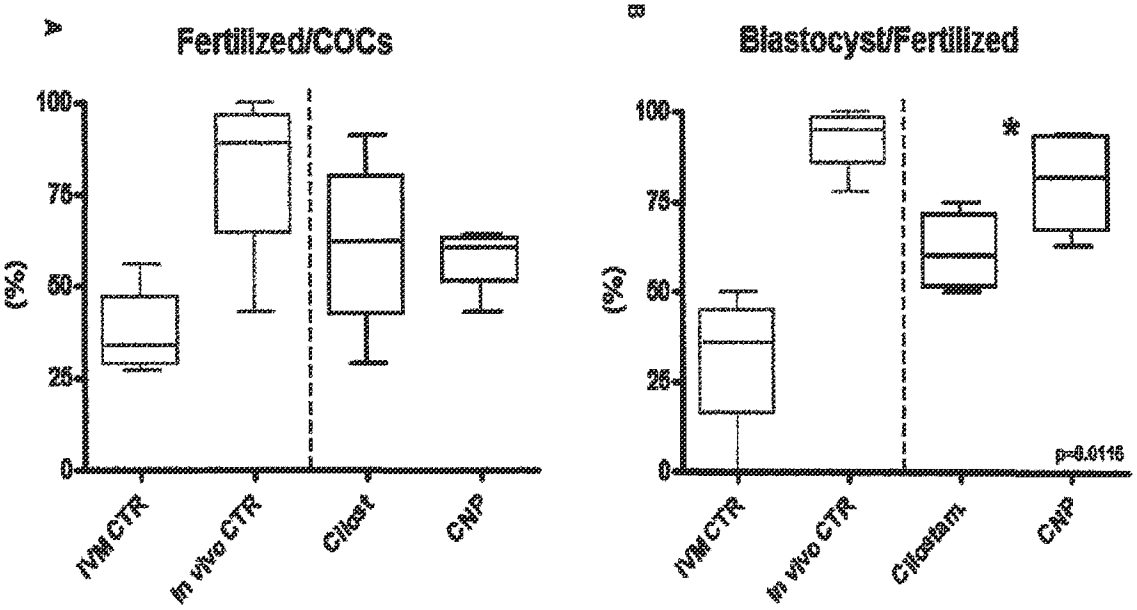

FIG. 8: Differential effects of CNP and PDE3I present during a capacitation culture on the developmental competence of mouse cumulus-enclosed oocytes from early antral follicles Rates of fertilization (A) and blastocyst formation (B) after capacitation culture followed by IVM. In both cases, data from two reference controls were included: 1) A control for IVM without prior capacitation culture & 2) A standard in-vivo control (fully-grown mature oocytes).

Figure 9:
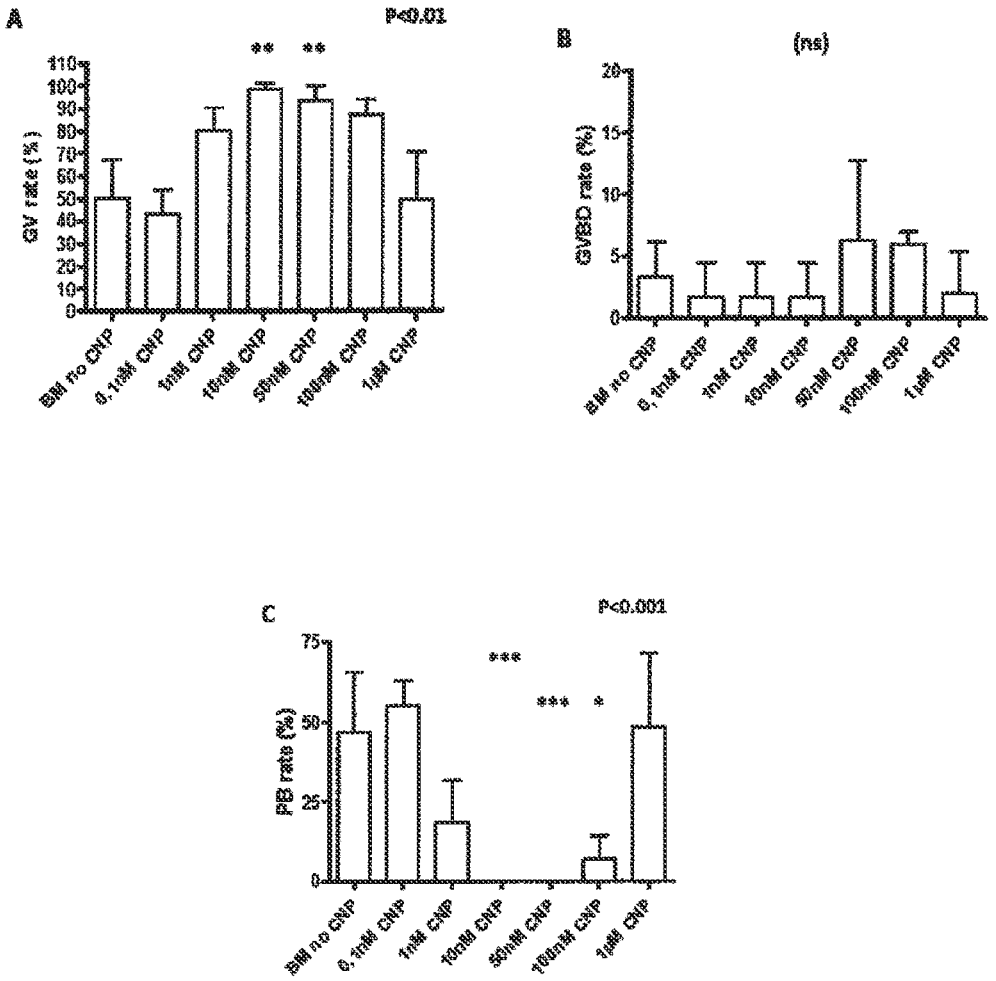

FIG. 9: Meiotic resumption after 18 hours. Dose dependent effect of CNP-22 on the progression of meiotic maturation. Preovulatory COCs were cultured in presence of CNP doses ranging 0.1 nM to 1 μM. A control condition (Basal Medium without CNP) was included. Each bar represents mean±SD of experimental data obtained from three replicates (on average, 54 oocytes/treatment). Asterisks indicate significant differences against the control condition without CNP (P<0.01). Panel A provides the percentage of oocytes with intact germinal vesicles (GV) rate (%) wherein the presence of intact GVs is indicative for meiotic arrest. Panel B provides the percentage of oocytes at the germinal vesicle breakdown (GVBD)-stage, expected to be low in case of meiotic arrest and Panel C provides the percentage of oocytes extruding the first polar body (PB), again expected to be low in case of meiotic arrest.

Figure 10:
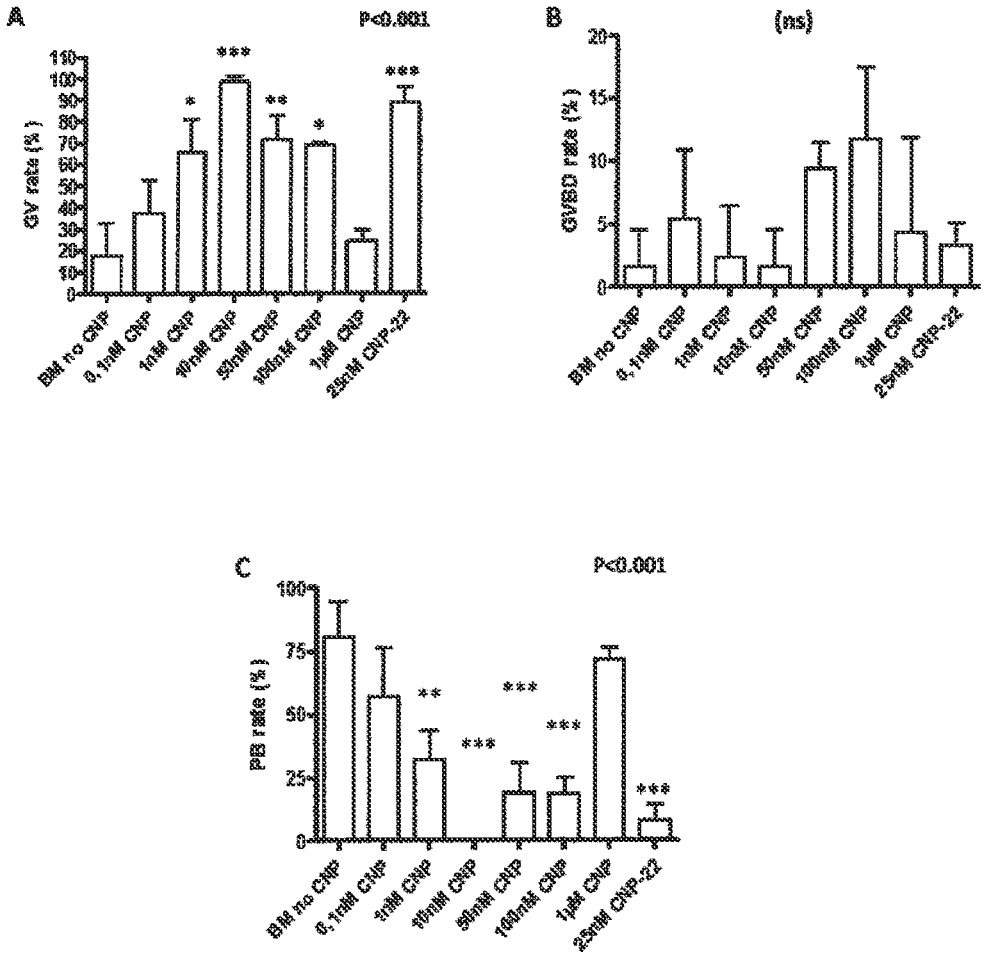

FIG. 10: Meiotic resumption after 18 hours. Dose dependent effect of CNP-53 on the progression of meiotic maturation. Preovulatory COCs were cultured in presence of CNP doses ranging 0.1 nM to 1 μM. A control condition (Basal Medium without CNP and a positive control with 25 nM CNP-22) was included. Each bar represents mean±SD of experimental data obtained from three replicates (on average, 54 oocytes/treatment). Asterisks indicate significant differences against the control condition without CNP (P<0.01). Panel A provides the percentage of oocytes with intact germinal vesicles (GV) rate. Panel B provides the percentage of oocytes at the germinal vesicle breakdown (GVBD)-stage. Panel C provides the percentage of oocytes extruding the first polar body (PB).

Figure 11:
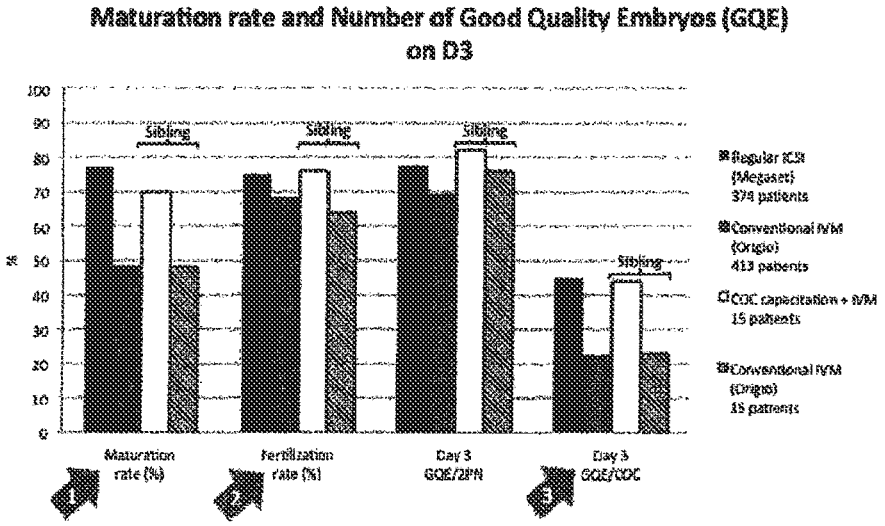

FIG. 11: Maturation rates, Fertilization rates and number of Good Quality Embryos (GQE) expressed per number of fertilized eggs (2PN) or per number of initial COCs (COC). Black bar (N=374 patients) : results from the 'conventional IVF(ICSI) field': reflects current ICSI practice in Europe. This data are obtained from the most frequently used stimulation therapy (GnRH antagonist+HP-hMG) embryology data from the published 'MEGASET' data: European Multi-Center Multinational study by Ferring Pharmaceuticals, where all embryos were cultured up to the blastocyst stage. Grey Bar (N=413 patients): results obtained with routine IVM (Origio Kit), when obtaining oocytes from NON-HCG triggered cycles. White Bar (N=15): results with the "New capacitation culture" step used on the oocytes from 15 patients that gave also COC for capacitation culture. Striped white Bar (N=15 patients): these results are from the routine IVM (Origio® method) on a part of the oocytes from 15 patients that gave COCs for capacitation culture (i.e. "sibling" with Green group).

Figure 12:
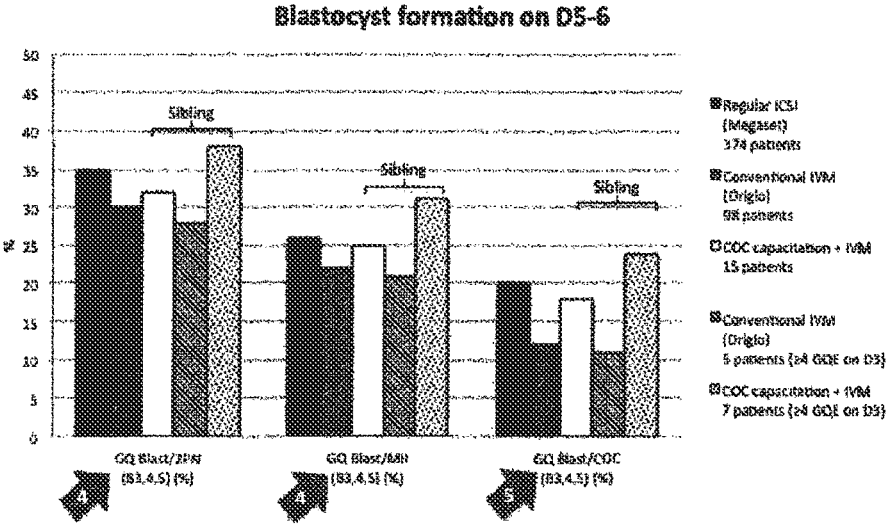

FIG. 12: Blastocyst formation on D5-D6, expressed per number of fertilized eggs (2PN), expressed per Mil Oocytes or per number of initial COCs (COC). Black bar (N=374 patients) results from the 'conventional IVF(ICSI) field': reflects current ICSI practice in Europe. This data are obtained from the most frequently used stimulation therapy (GnRH antagonist+HP-hMG) : embryology data from the published 'MEGASET' data: European Multi-Center Multinational study by Ferring Pharmaceuticals, where all embryos were cultured up to the blastocyst stage. Grey Bar (N=98 patients): is results from the subgroup of 98 patients, whose embryos are only further cultured into blastocyst medium if they had 4 or more good Day3 embryos. White Bar (N=15): results with the "New capacitation culture" step used on the oocytes from 15 patients that gave also COC for capacitation culture. Striped white Bar (N=5 patients): is results from the subgroup of 5 patients, whose embryos are only further cultured into blastocyst medium if they had 4 or more 'good quality' Day3 embryos. NOTE: This is the most favorable 'bias' for the routine IVM . Dotted white Bar (N=7): are results from the subgroup of 7 sibling patients with the "New capacitation culture" step; i.e. embryos are only considered for their development in blastocyst medium in case they had 4 or more 'good quality' Day3 embryos. NOTE : This subgroup analysis was done to make the ideal comparison to the policy of blastocyst culture in routine IVM (stripped white bar).

DETAILED DESCRIPTION OF THE INVENTION

The present invention is directed to compositions and methods for assisted reproductive technology in mammals. Specifically, the invention relates to compositions and methods for in vitro maturation of a mammalian cumulus oocyte complex (COC). The invention is based on the finding that the combination of a low dose of CNP, estradiol and FSH successfully allows in vitro maturation of early antral follicles, in particular the small early antral follicles with a diameter below 9 mm.

The term 'follicle', as used herein, refers to an ovarian follicle that is the basic unit of female reproductive biology and is composed of roughly spherical aggregations of cells found in the ovary. A follicle contains a single oocyte. Follicles are periodically initiated to grow and develop, culminating in ovulation of usually a single competent oocyte. The cells of the ovarian follicle are the oocyte, granulosa cells, and the cells of the internal and external theca layers.

The term 'oocyte', as used herein, includes an oocyte alone or an oocyte in association with one or more other cells, such as an oocyte as part of a cumulus oocyte complex (COC). The nucleus of an oocyte is called germinal vesicle.

The term 'cumulus cell', as used herein, refers to a cell in the developing ovarian follicles, which is in direct or close proximity to an oocyte. Cumulus cells are involved in providing an oocyte some of its nutritional, energy and/or other requirements that are necessary to yield a viable embryo upon fertilization.

The term 'cumulus oocyte complex', as used herein refers to at least one oocyte and at least one cumulus cell in a physical association with each other. In general the oocyte is surrounded by tightly packed layers of cumulus cells, thereby forming the cumulus oocyte complex.

Assisted reproduction technology or ART as used herein, includes all fertility treatments in which both female gametes (oocytes) and male gametes (sperm) are handled. In vitro fertilization (IVF) is one of several assisted reproductive techniques used to assist infertile couples in conceiving a child. IVF refers to the procedure by which oocytes are removed from the female's ovary and fertilized with sperm in a laboratory procedure.

While in the conventional ART, gonadotropins are used to stimulate the ovary to produce many large follicles with mature oocytes in vivo, IVM aims primarily to avoid the side effects of ovarian stimulation by retrieving immature oocytes from small follicles (diameter <12 mm) from unstimulated or minimally stimulated ovaries. However, the intrinsic developmental competence of oocytes is reduced after IVM compared with conventional ART.

Nuclear maturation of an oocyte encompasses the processes reactivating meiosis arrest at prophase I and stimulates the meiotic process to proceed to metaphase II (MII-stage), at which stage fertilization usually takes place. Oocytes arrested in prophase I exhibit a so-called germinal vesicle (GV-stage), in which the nuclear membrane and the nucleolus are visible through a microscope. Nuclear maturation becomes manifest when the oocyte undergoes the so-called GV breakdown (GVBD stage), progress to the MII-stage and extrude the first polar body (PB). Cytoplasmic maturation refers to the processes that prepare the oocyte for activation, formation of pronuclei and the developmental path undertaken until implantation has been accomplished. The competence to undergo both nuclear and cytoplasmic maturation of GV-stage oocytes is usually acquired in a stepwise manner.

Oocyte in vitro maturation (IVM) is a technique that enables to mature GV—stage oocytes (such as COCs) that are enclosed in a firmly condensed corona cumulus layer. These oocytes can be obtained by ultrasound-guided needle puncture before or after ovulation has been triggered by administration of human chorionic gonadotrophin (hCG). Oocyte IVM has the potential to simplify fertility treatment or to reduce risks and costs related to hormone (hCG) stimulation in patients with normal or high ovarian follicular reserve. This follicular reserve is routinely determined by measurement of the anti-müllerian hormone (AMH) levels and by ultrasound-guided follicle count on day 3 of the menstrual cycle.

The success of ART and IVM depends to a large extent on the maturity of the oocyte prior to fertilization. Oocytes harvested from antral follicles typically undergo spontaneous resumption of meiosis, i.e. proceed to nuclear maturation, when placed in culture. This nuclear maturation may often occur before the oocyte has undergone complete cytoplasmic maturity. This is believed to ultimately affect the success of fertilization and possibly subsequent embryo development and implantation. Therefore, the main challenge for IVM is synchronization of nuclear and cytoplasmic maturation processes within the oocyte. A prolonged oocyte maturation period would promote a longer interaction between the immature oocyte with adequately conditioned cumulus cells. In addition, IVM of small follicles seems to be even more challenging. It is known from literature that small human follicles do not express sufficient amounts of LH receptor and/or the receptor system for EGF and EGF-like factors-. Consequently the principal cascade of EGF-like factors, which induces maturation, cannot be activated.

In the present invention, the immature mammalian COC is collected without prior hCG stimulation or only after hCG stimulation. In a preferred embodiment, hCG stimulation has not occurred before COC collection. In an even more preferred embodiment, any trigger, including high doses of FSH, LHRH, recombinant LH or LH analogs has to be avoided prior collection of COCs in vivo.

The present invention is based on the finding that a specific range of 'low' doses of C-type natriuretic peptide (CNP) in combination with estradiol and FSH markedly Improves the IVM process of mammalian COCs, in particular those derived from small early antral follicles with a diameter below 9 mm. As further evident from the examples hereinafter, and clearly different from the application of PDE3 inhibitors to maintain COCs in meiotic arrest, CNP has a bell shaped dose curve. Unexpectedly, not only very low doses as 0.1 nM, but also very high doses as 1 μM demonstrated to be suboptimal in maintaining oocytes arrested at the GV stage. This difference in dose curve implies different underlying mechanisms, rendering CNP treatment to go beyond simply delaying the start of meiotic resumption in small early antral follicles as further detailed hereinafter.

It is accordingly a first aspect of the present invention to provide a capacitation medium for in vitro maturation of a mammalian COC. The capacitation medium comprises 0.1 to 50 nM C-type [natrluretic] *natriuretic* peptide (CNP), estradiol and FSH. In a specific embodiment, the capacitation medium comprises 1 to 1000 nM estradiol. In another embodiment, the capacitation medium comprises 0.1 to 10 *mIU/ml* of FSH. In yet another aspect, the capacitation medium comprises equipotent doses of recombinant FSH, FSH analogs, or FSH mimetic molecules. In yet another embodiment, the capacitation medium comprises 0.1-10 ng/ml insulin. In another aspect, the capacitation medium comprises equipotent doses of insulin analogs or insulin mimetic molecules. In yet another embodiment, the capacitation medium comprises 0.1 to 50 nM CNP, preferably 10-50 nM CNP, most preferably 10-25 nM CNP, even more preferably 25 nM CNP; 1 to 1000 nM estradiol, most preferably 10 nM estradiol; 0.1 to 10 [mIU/ml] *mIU/ml* FSH, most preferably 2.5 or 1 [mIU/ml] *mIU/ml* FSH; and 0.1 to 10 ng/ml insulin, most preferably 5 ng/ml insulin. Furthermore, in some embodiments of the invention, the capacitation medium comprises an oocyte-secreted factor or a combination of oocyte-secreted factors. The oocyte-secreted factors as used herein are selected from the group consisting of GDF-9, BMP-15, FGF-8 or any combination thereof. In a particular embodiment, the oocyte-secreted factors are recombinant proteins. In yet another aspect, the oocyte-secreted factors are heterodimeric proteins. In yet another further embodiment, the capacitation medium preferably comprises 0.1 to 50 nM CNP, preferably 10-50 nM CNP, most preferably 10 to 25 nM CNP, even more preferably 25 nM CNP; 1 to 1000 nM estradiol, even more preferably 10 nM estradiol; 0.1 to 10 [mIU/ml] *mIU/ml* FSH, even more preferably 2.5 or 1 [mIU/ml] *mIU/ml* FSH; 0.1 to 10 ng/ml insulin, even more preferably 5 ng/ml insulin; and an oocyte-secreted factor selected from the group consisting of GDF-9, BMP-15, FGF-8 or any equivalent or combination thereof.

The atrial natriuretic peptide (ANP), brain natriuretic peptide (BNP) and C-type natriuretic peptide are the most studied members of the family of the natriuretic peptides. CNP is encoded by the Natriuretic peptide precursor C (NPPC) gene, which is expressed in diverse cell types in which the precursor NPPC protein is cleaved into the 22 amino acid peptide CNP. CNP activates its cognate receptor guanylyl cyclase B (GC-B), also known as natriuretic peptide receptor-B (NPRB), whereas ANP and BNP stimulate guanylyl cyclase (GC-A), also known as natriuretic peptide receptor-A (NPRA). GC-A and GC-B are membrane-anchored guanylyl cyclase enzymes that signal via the production of the second messenger cGMP. CNP acts in an autocrine/paracrine fashion to induce vaso-relaxation and vascular remodeling, and to regulate bone growth.

CNP is 22 amino acid residues in length (CNP-22), and an N-terminally elongated form with 53 amino acid residues (CNP-53) has also been described. ANP, BNP and CNP are highly homologous with the 17-residue ring structure formed by an intramolecular disulphide linkage. The genetic sequence for the NPPC gene may be accessed at Genbank, locus NM_024409. ANP and BNP act mainly as cardiac hormones, produced primarily by the atrium and ventricle, respectively. CNP was thought to be expressed mainly in the brain. However, other studies demonstrated production of CNP by cultured endothelial cells and by blood vessels in vivo with augmentation of production of CNP by various cytokines and growth factors. Studies have reported ovarian expression of NPPC and NPRB and their regulation by gonadotrophins. A recent study demonstrated the expression of NPPC mRNA in granulosa cells and the ability of CNP to stimulate cGMP production in cumulus cells. cGMP then diffuses via gap-junctions from the cumulus cells to the oocytes and prevents phosphodiesterase type 3 (PDE3)-dependent cAMP degradation, therefore maintaining oocytes under meiotic arrest.

As will become apparent from the examples hereinafter, the combination of a low dose of CNP with estradiol and FSH is essential to prolong the CNP-induced meiotic arrest. CNP efficiently maintains meiotic arrest in COCs for at least 24 hours, but CNP alone was insufficient to maintain meiotic arrest for 48 hours. Therefore, CNP alone does not allow NM of small early antral follicles, for which a long-term in vitro culture period is essential for successful maturation. However, the combination of a low dose of CNP with estradiol allowed the COC to maintain meiotic arrest for a long period, although the final embryo quality of the oocyte after IVF was not sufficient. Furthermore, supplementation of FSH to the capacitation medium in addition to CNP and estradiol, also maintained the COC in meiotic arrest for a long period. Moreover, supplementation of FSH improved meiotic resumption, increased the oocyte diameter and improved the embryo quality after IVF procedure.

FSH is a hormone synthesized and secreted by gonadotropes in the anterior pituitary gland. FSH regulates the development, growth, pubertal maturation, and reproductive processes of the human body, FSH and Luteinizing Hormone (LH) act synergistically in reproduction. In the ovary, FSH stimulates the growth of immature follicles to maturation. As the follicle grows, it releases inhibin, which blocks the FSH production. FSH is a dimeric glycoprotein. The alpha subunits of LH, FSH, TSH, and hCG are identical, and contain 92 amino acids. FSH has a beta subunit of 118 amino acids that confers its specific biologic action and is responsible for interaction with the FSH receptor.

For clinical use, various formulations are available. It is used commonly in infertility therapy to stimulate follicular development. FSH is available mixed with LH or hCG in the form of for example Pergonal or Menopur, which are urinary purified gonadotropins, as well as in pure forms as recombinant FSH (for example Gonal F, Puregon), and as for example Gonal-F, Gonal-f RFF, Gonal-f RFF Pen. Analogs of FSH are also clinically useful and include all biologically active mutant forms, e.g. where one, two, three or more amino acids are altered from the native from, PEGylated FSH, single chain bi-functional mutants, FSH-CTP, and the like. Also long-acting FSH therapies have been developed, including an FSH-CTP (Corifollitropin alfa, where the FSH beta subunits are linked by the C-terminal peptide (CTP) moiety from hCG) such as Elonva.

Insulin is a hormone central to regulate carbohydrate and fat metabolism in the body. In target cells, insulin initiates a signal transduction through the activation of membrane receptors with tyrosine kinase activity. This signal transduction results in increased glucose uptake and storage. Also in oocytes, the insulin signaling cascade is active. Insulin acts synergistically with FSH in promoting granulosa cell differentiation and function. For clinical use, also recombinant insulin is available. Insulin is used in the clinic as part of a Synthetic Serum Replacement (SSR). SSR is a media component widely used in different media for embryo culture.

Oocyte-secreted factors are paracrine factors secreted by the oocyte and necessary for normal granulosa cell and thecal cell function. The term "oocyte-secreted factors" as used herein is to be understood to mean factors secreted by an oocyte that act upon a granulosa cell to regulate key functions in granulosa cells, such as proliferation, differentiation, glucose metabolism and cholesterol biosynthesis. Oocyte-secreted factors are selected from the group consisting of GDF-9, BMP-15, FGF-8, or any equivalent thereof. GDF-9 is a member of transforming growth factor β superfamily. Oocyte expression of GDF-9 begins at the primary follicle stage and persists through ovulation. As used herein, "GDF-9" refers to GDF-9 protein, its individual subunits, multimers of its individual subunits, functional fragments or portions of GDF-9, and functional equivalents and/or analogues of GDF-9. As defined herein, functional equivalents or fragments of "GDF-9" included modified GDF-9 protein such that the resulting GDF-9 product has activity similar to GDF-9.

BMP-15 is a member of the transforming growth factor beta (TGF-β) superfamily. It is synthesized as prepropeptide, cleaved, and then processed into dimeric proteins. BMP-15 may form homodimers, and also heterodimers with GDF-9. As used herein, "BMP-15" refers to BMP-15 protein, its individual subunits, multimers of its individual subunits, functional fragments or portions of BMP-15, and functional equivalents and/or analogues of BMP-15. As defined herein, functional equivalents or fragments of "BMP-15" included modified BMP-15 protein such that the resulting BMP-15 product has activity similar to BMP-15.

FGF-8 is a member of the fibroblast growth factor (FGF) family. In adult ovaries, FGF-8 is expressed in oocytes and expression of FGF receptors was reported in granulosa cells. During oocyte maturation, FGF-8, together with other oocyte-secreted factors, promotes glycolysis in cumulus cells. As used herein, "FGF-8" refers to FGF-8 protein, its individual subunits, multimers of its individual subunits, functional fragments or portions of FGF-8, and functional equivalents and/or analogues of FGF-8. As defined herein, functional equivalents or fragments of "FGF-8" included modified FGF-8 protein such that the resulting FGF-8 product has activity similar to FGF-8.

In another embodiment, the capacitation medium comprises CNP, estradiol and FSH in combination with one or a combination of oocyte-secreted factors, selected from the group consisting of GDF-9, BMP-15, FGF-8 or any combination thereof. This combination of growth factors and hormones significantly improves the developmental competence and the final embryo quality of oocytes derived from small antral follicles, as evidenced in the examples described herein below. in particular, addition of GDF-9 to the capacitation medium promoted oocyte chromatin configuration remodelling into a condensed stage, oocyte diameter and oocyte and embryo quality.

Another aspect of the present invention is the use of a capacitation medium, as described herein above, for in vitro maturation of immature mammalian COCs. Said use comprises contacting the mammalian COC with the capacitation medium for a period of minimum 2 h and maximum 96 h. In particular, the COC is contacted with the capacitation medium for a time sufficient to reach an advanced stage of development, as evidenced for example by reorganization of oocyte's chromatin into a condensed stage or the so-called surrounded nucleolus (SN) configuration. In a further particular embodiment, the mammalian COC is contacted with the capacitation medium for a period determined by the size of the follicle.

The use of the capacitation medium comprising CNP, estradiol and FSH induces meiotic arrest in the immature mammalian COC. Typical for the present invention and as evidenced from the examples hereinafter, the use of a capacitation medium comprising CNP, estradiol and FSH enables a prolonged 'capacitation' culture of oocytes, up to 96 h. As a result, this prolonged period of meiotic arrest allows oocytes from small follicles to survive, to grow and to reach [an] *a* further advanced stage of development with the aim of obtaining a higher capacity for reproduction. So far, in vitro maturation of these small follicles has been challenging because the culture conditions and time during which the oocytes could survive under meiotic arrest was too short to acquire full nuclear and developmental competence. As further shown in the example, without CNP oocytes from the smallest size of follicles spontaneously resumed meiosis. In contrast, when treated with 1 nM, 10 nM, 25 nM, or 50 nM CNP almost 100% of the oocytes could be maintained in meiotic arrest.

Not only does the capacitation medium of the present invention enable a prolonged culture of oocytes, the presence of CNP equally sustains cumulus-oocyte connections with a notable improvement on the oocyte's development capacity, especially when compared to the present use of PDE3 inhibitors in maintaining COCs in meiotic arrest.

After the use of a capacitation medium as described herein, oocytes will be able to reach an advance developmental stage. Oocyte's chromatin configuration is evaluated in GV oocytes by staining with Hoechst and analysis under a fluorescence microscope. Chromatin configuration is classified as non-surrounded nucleolus (NSN), surrounded nucleolus (SN), or transitional (NSN/SN) stage, according to the pattern of chromatin aggregation around the nucleolus. Also the diameter of the oocytes is recorded prior to staining with Hoechst. Furthermore, after the capacitation period, meiotic competence can be induced and analyzed by assessing the nuclear maturational stage under an inverted microscope. Nuclear maturation of oocytes is scored as GV (germinal vesicle) stage, GVBD (germinal vesicle breakdown) stage and Mil (metaphase)- or PB (polar body). As oocytes grow, they acquire the competence to reinitiate meiosis, a process also called meiotic resumption. At that stage, oocytes undergo breakdown of the germinal vesicle membrane and chromosomes separate from one another.

In the present invention, the COC is contacted with the capacitation medium for a time sufficient to reach an advanced stage of development, as evidenced for example by reorganization of oocyte's chromatin into a condensed stage or the SN configuration. Furthermore, the mammalian COC is contacted with the capacitation medium for a period determined by the size of the follicle. Follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mar are preferred to stay for at least 2 h in the capacitation medium.

In another embodiment, the use of the capacitation medium is part of an assisted reproductive technology, in particular in vitro fertilization and ICSI.

The invention also provides an in vitro method for maturation of an immature mammalian COC. In said method, an immature COC is collected in collection medium and contacted with the collection medium for minimally 30 minutes to maximally 2 hours. Also in said method, and after contacting with the collection medium, the mammalian COC is contacted with a capacitation medium as described above to maintain meiotic arrest and promote cumulus-oocyte interactions. Finally, the mammalian COC is further contacted with a maturation medium to allow meiotic maturation of the oocyte.

In a specific embodiment, in the method according to the present invention, the immature COC is contacted with the collection medium for minimally 30 minutes to maximally 2 hours.

Said collection medium comprises natural or man-made pharmacological compounds inhibiting naturally occurring phosphodiesterases or natural inhibitors of oocyte meiotic resumption, generally referred to as meiotic arresters. Said natural inhibitors may be selected from the group consisting of CNP, hypoxanthine or analogs thereof. The use of this collection medium allows the retrieval of COCs from very small antral follicles without obligatory need of ovarian stimulation at any moment of the oestrus or menstrual cycle, The presence of such meiotic arrester in the collection medium has the purpose of blocking the decrease of cAMP from the collected COCs, in particular to prevent re-initiation of meiosis in those that have the capacity to do so, i.e. those that are nuclear mature- and also to keep the conditions 'right' for the interconnections between oocyte and cumulus. Said collection medium is to be used during COC collection, as medium where the punctured COC is transferred in from the puncture needle. The COC freshly detached stays preferably for minimally 30 minutes to maximally 2 hours in this collection medium. The main purpose of this collection medium is to keep the COC in an optimal functional status while they are separated from follicular fluid and other contaminating cells. The COC is isolated as separate entities to be transferred to the "capacitation medium".

In another embodiment of the in vitro method according to the invention, the mammalian COC is contacted with a capacitation medium as described above. In said method, the mammalian COC is contacted with the capacitation medium comprising CNP, estradiol and FSH for a period of minimum 2 h to maximum 96 h. In particular, in the in vitro method for maturation, the COC is contacted with the capacitation medium for a time sufficient to reach an advanced stage of development, as evidenced for example by reorganization of oocyte's chromatin into a condensed stage or the so-called surrounded nucleolus (SN) configuration. Even more in particular, in the in vitro method for maturation, meiotic re-initiation is analyzed by assessing the nuclear maturational stage under an inverted microscope. Nuclear maturation of the oocyte is scored as GV (germinal vesicle) stage, GVBD (germinal vesicle breakdown) stage, and MII (metaphase)- or PB (polar body) stage. In a further particular embodiment, the mammalian COC is contacted with the capacitation medium for a period determined by the size of the follicle. As already described herein, follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least 2 h in the capacitation medium.

In a particular embodiment, the mammalian COC is contacted with the capacitation medium in a non-adherent or adherent culture plate. As will become apparent from the examples hereinafter, the combination of a low dose of CNP with estradiol and FSH is essential to prolong the CNP-mediated meiotic arrest CNP efficiently maintains meiotic arrest in COCs for at least 24 hours, but CNP alone was insufficient to maintain meiotic arrest for 48 hours. However, the combination of a low dose of CNP with estradiol allowed the COCs to maintain meiotic arrest for a long period, although the final embryo quality of these oocytes after IVF was not high enough. Supplementation of FSH to the capacitation medium in addition to CNP and estradiol also maintained the COCs in meiotic arrest for a long period but it also increased the oocyte diameter and improved the embryo quality after IVF procedure.

In another embodiment, in the in vitro method according to the present invention, the oocyte-secreted factors, such as GDF-9, BMP-15, FGF-8 or any combination thereof are added to the capacitation medium comprising CNP, estradiol and FSH. Similar to FSH, these oocyte-secreted factors improve the developmental competence of oocytes of small antral follicles, and their final embryo quality.

As already mentioned herein before, in the in vitro method of the present invention, the COC is further contacted with a maturation medium. At that stage, and given the use of the capacitation media according to the present invention, the capacitated cumulus-enclosed GV-stage oocyte can be matured in a maturation medium with any basal composition that is supplemented with a selection of growth factors. These growth factors are selected from a group consisting of, but not limited to, EGF-like factors such as Amphiregulin or Epiregulin, FSH, LH, CAMP modulators, or a combination thereof. Thus in a further embodiment the in vitro maturation method of the present invention comprises contacting a COC with a capacitation medium as described herein, and contacting a COC with a maturation medium, characterized in that the maturation medium is consisting of any basal composition supplemented with a selection of growth factors as described herein.

It is also an object of the present invention to provide a kit for in vitro maturation of an immature mammalian COC. Said kit comprises a capacitation medium as described herein and comprising 0.1 to 50 nM CNP, estradiol and FSH. In a particular embodiment, the kit according to the present invention comprises a capacitation medium comprising 1 to 1000 nM estradiol. In another embodiment, the kit comprises 0.1 to 10 *mIU/ml* FSH. In yet another aspect, the capacitation medium comprises equipotent doses of recombinant FSH, FSH analogs, or FSH mimetic molecules. In yet another embodiment, in the kit according to the present invention the capacitation medium comprises 0.1 to 10 ng/ml insulin. In another aspect, the capacitation medium comprises equipotent doses of insulin analogs or insulin mimetic molecules. In another embodiment, in the kit according to the present invention, the capacitation medium comprises 0.1 to 50 nM CNP, preferably 10 to 25 nM CNP, even more preferably 25 nM CNP; 1 to 1000 nM estradiol, preferably 10 nM estradiol; 0.1 to 10 [mIU/ml] *mIU/ml* FSH, preferably 2.5 or 1 [mIU/ml] *mIU/ml* FSH; and 0.1 to 10 ng/ml insulin.

In a further embodiment, in a kit according to the present invention, the capacitation medium comprises an oocyte-secreted factor. The oocyte-secreted factors used herein are selected from the group consisting of GDF-9, BMP-15, FGF-8 or any combination thereof. In a particular embodiment, the oocyte-secreted factors used herein are recombinant proteins or heterodimeric proteins. in another embodiment, the kit for in vitro maturation of an immature mammalian COC comprises (a) a collection medium comprising natural or man-made chemical compounds inhibiting naturally occurring phosphodiesterases or natural inhibitors of oocyte meiosis, (b) a capacitation medium as described above, (c) a maturation medium, (d) adherent and non-adherent culture plates, and (e) instructions for use of the kit. The kits, as described herein, may be useful in performing the methods described herein together with instructions for carrying out the methods, which are included in the kit.

Another aspect of the present invention discloses the use of a kit for in vitro maturation of a mammalian COC, as described herein above. In a particular embodiment, the use of a kit comprising a capacitation medium as described herein above is disclosed. This use comprises contacting the mammalian COC with the capacitation medium for a period of minimum 2 h to maximum 96 h. More in particular, in the use of a kit comprising a capacitation medium, the mammalian COC is contacted with the capacitation medium to maintain meiotic arrest and to allow nuclear and cytoplasmic maturation. In particular, the COC is contacted with the capacitation medium for a time sufficient to reach an advanced stage of development, as evidenced for example by chromatin remodeling into a surrounded nucleolus (SN). In a further particular embodiment, the mammalian COC is contacted with the capacitation medium for a period determined by the size of the follicle. As already described herein, follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least for 2 h in the capacitation medium.

The capacitation period enables the oocyte to gain competence to resume meiosis, which is only evaluated after the meiotic stimulus is triggered, for instance, the contact with a maturation medium. Assessment of oocyte nuclear maturation is performed under inverted microscope and evidenced by the breakdown of the germinal vesicle (GVBD) and further extrusion of the first polar body (PB).

In another embodiment, the use of a kit comprising (a) a collection medium comprising natural or man-made chemical compounds inhibiting naturally occurring phosphodiesterases or natural inhibitors of oocyte meiosis, (b) a capacitation medium as described above, (c) a maturation medium, (d) adherent and/or non-adherent culture plates, and (e) instructions for use of the kit is disclosed. Typical, the use of the kit for in vitro maturation of an immature mammalian COC comprises contact of the COC with the collection medium for minimally 30 minutes to maximum 2 hours. In another aspect, in the use of a kit according to the present invention, the mammalian COC is contacted with the capacitation medium for a period of minimum 2 h to maximum 96 h. More in particular, in the use of a kit comprising a collection medium, a capacitation medium, a maturation medium, adherent and/or non-adherent culture plates and instructions for use, the mammalian COC is contacted with the capacitation medium to maintain meiotic arrest and to allow maturation. In particular, the COC is contacted with the capacitation medium for a time sufficient to reach the GVBD stage and reinitiate meiosis, thereby reaching an advanced stage of development, as evidenced for example by a surrounded nucleolus (SN). In addition, the mammalian COC is contacted with the capacitation medium for a period determined by the size of the follicle. As already described herein, follicle size is determined at the moment of COC retrieval such as for example by ultrasound imaging. Follicles with a diameter of 1 to 5 mm are preferred to stay for at least 48 h in the capacitation medium. Follicles with a diameter of >5 to 10 mm are preferred to stay for at least 24 h in the capacitation medium, and follicles with a diameter of more than 10 mm are preferred to stay for at least 2 h in the capacitation medium.

The capacitation period enables the oocyte to gain competence to resume meiosis, which is only evaluated after the meiotic stimulus is triggered, for instance, the contact with a maturation medium. Assessment of oocyte nuclear maturation is performed under inverted microscope and evidenced by the breakdown of the germinal vesicle (GVBD) and further extrusion of the first polar body (PB).

Within the different embodiments of the invention, the mammalian COC is a human COC.

Other aspects of the present invention are well known in the art. For example, methods for obtaining oocytes from a subject, the tools and equipment for manipulating oocytes, cryopreservation methods, IVF methods—in vitro embryo culture, and methods for placement of embryos in a patient's reproductive tract are well-known in the are and any such suitable methods known in the art can be used in conjunction with the methods and compositions of the present invention.

The present invention may be further illustrated by way of the following non-limiting examples.

EXAMPLES

Example 1

Materials and Methods

Animal Model

Animals used for the current study were CBAB6F1 (F1 hybrids of C57B1/6j×CBA/ca). These animals were housed and bred following the national legislation and with the consent of the ethical committee of the Vrije Universiteit Brussel (Project number: 09-216-1).

Collection of Immature Cumulus-oocyte Complexes (COCs) from Small Antral Follicles and Pre-ovulatory COCs from Large Antral Follicles For the collection of immature COCs, compact COCs of the first wave of follicular development were collected from small antral follicles of pre-pubertal mice (19-21 days-old), without prior gonadotropin administration. For the collection of pre-ovulatory COCs (controls), compact COCs were collected by puncturing large antral follicles of pre-pubertal female mice (25-27 days-old) following 48 hrs of priming with [2,5IU] *2.5 IU* equine Chronic Gonadotropin (eCG, Folligon, Intervet, Oss, The Netherlands). Collection medium consisted of Leibovitz L-15, containing 10% Heat-inactivated Foetal Bovine Serum (FBS), [100IU/ml] *100 IU/ml* penicillin, 100 μg/ml streptomycin (all from Life Technologies, Gent, Belgium) and supplemented with 200 μM 3-Isobutyl-1-methylxanthine (IBMX; Sigma, Schnelldorf, Germany) to prevent meiosis reinitiation during the period of collection and pre culture handling.

Culture of COCs

Basal culture medium for the culture of COCs (Pre-IVM and IVM phases) consisted of α-MEM, 2.5% FBS (both from Life Technologies, Gent, Belgium) and 5 ng/mL Insulin, 5 [ug/mt] *ug/ml*. Apo-Transferrin, 5 ng/mL Sodium selenite (All from Sigma, Schnelldorf, Germany).

For Pre-IVM experiments, CNP-22 was obtained from Phoenix Europe (Karlsruhe, Germany), 17-β-estradiol from Sigma, (Schnelldorf, Germany), and Growth and Differentiation Factor 9 (GDF9) from R&D systems Europe (Oxon, United Kingdom).

For experiments involving IVM, recombinant Epidermal growth Factor (r-EGF) (Roche; Mannheim, Germany) and recombinant mouse Epiregulin (EREG) (R&D systems Europe; Oxon, United Kingdom) were used as ovulatory stimuli and the cultures lasted 18 hrs.

Where mentioned recombinant Follicle Stimulating Hormone (FSH) (Merck-Serono, Geneva, Switzerland) was added to Pre-IVM and IVM media.

Assessment of Meiotic Reinitiation

At specified time-points oocytes were mechanically freed from compact or expanded cumulus cells by using a mouth controlled fine bore glass pipette. Meiotic reinitiation was analyzed by assessing the nuclear maturational stage under an inverted microscope equipped with a Hoffman modulation contrast system (Nikon, Tokyo, Japan). Nuclear maturation was scored as GV (Germinal vesicle stage), GVBD (when GV non visible), PB (first polar body observed in perivitelline space) or DEG (when the oocyte was degenerated).

Evaluation of Oocyte's Chromatin Configuration

Oocyte's chromatin configuration was evaluated in Germinal Vesicle oocytes, before and after Pre-IVM culture. Briefly, after assessment of meiotic reinitiation, GV oocytes were stained with 10 μg/mL Hoechst 33258 (Sigma; Schnelldorf, Germany) for 5 minutes. Nucleolar chromatin configuration was analyzed under a fluorescence microscope (IX70; Olympus). Chromatin configuration was classified as non-surrounded nucleolus (NSN), surrounded nucleolus (SN), or transitional (NSN/SN) stage, according to the pattern of chromatin aggregation around the nucleolus [27-29]. The diameters of some of these oocytes were recorded prior to staining with Hoechst.

In Vitro Fertilization Procedure (IVF)

In the ultimate test to assess oocyte's developmental competence, after Pre-IVM+IVM culture periods, in vitro fertilization (IVF) followed by embryo culture to the blastocyst stage was performed. For this experiment, 100 ng/mL EREG was used as trigger for meiotic resumption. Medium for IVF consisted of M16 medium, 3% Bovine serum albumin fraction V (BSA) (both from Sigma, Schnelldorf, Germany) and Non-essential amino acids (Life Technologies, Gent, Belgium). Embryo culture medium consisted of M16 medium and Essential and Non-essential amino acids (Life Technologies, Gent, Belgium).

Cumulus oocyte complexes were collected from the different conditions and washed once in IVF medium. In vitro fertilization was performed in IVF Medium using capacitated sperm (final dilution of $2\times10^6$ sperm/mL) obtained from a CBAB6F1 male. After 3.5 hours of co-incubation at 37° C., 5% CO2, 5% O2 and 100% humidity, presumptive zygotes were denuded, washed twice and cultured in groups of 10-15 zygotes in 20 μL of embryo culture medium overlaid with oil for embryo culture (Irvine Scientific, Alere; Sint Denijs Westrem, Belgium) at 37° C. in 5% CO2, 5% O2 and 100% humidity. Cleavage (2-cell) rate was scored 24 hours after IVF. On day 5, blastocyst development and hatching were recorded.

The competence of immature COCs from small antral follicles of mice aged 20 days-old, undergoing 18 hrs IVM with 100 ng/mL EREG was also evaluated.

In vivo grown oocytes (controls) were obtained from female aged 25-27 days-old primed for 48 h with 2.5IU of equine chorionic gonadotropin (eCG, Folligon®) followed by 14 hour with 2,5IU hCG (Chorulon®) (both from Intervet, The Netherlands). These oocytes were inseminated with same sperm sample and oocytes/embryos cultured under the exact same conditions as the IVM oocytes.

Statistical Analysis

Unless mentioned otherwise, the results are shown as the Mean±SD. Differences in the rate of oocyte meiotic resumption (per meiotic stage), chromatin configuration and embryo development following IVF, among the different in vitro conditions, were assessed by ANOVA followed by a Tukey's Multiple Comparison Test, $p<0.05$. Unpaired t-test was used to compare the rates of meiotic resumption when comparing 2 conditions. Percentages data were transformed (arcsine) before performing statistical analysis.

Results

CNP Efficiently Maintains Meiotic Arrest and Delays EGFR-dependent Meiotic Resumption Pre-ovulatory COCs, retrieved from gonadotropin-primed mice (aged 26-27 days-old), were placed in culture, for 18 hours, in presence of 0 (Control), 1, 10, 100 nM CNP-22 and in combination with 4 ng/mL EGF.

CNP-22 had a dose-dependent effect on the maintenance of meiotic arrest. At a dose of 100 and 10 nM the GV rate at the end of culture was significantly higher than at 1 nM and Control (96%, 93%, 48% and 0%) (FIG. 1A)

In *the* presence of EGF, a dose dependent effect of CNP-22 on the PB rate was observed. At a dose of 10 and 100 nM CNP-22 many oocytes remained at the GVBD stage, and therefore the PB rate remained significantly lower (35% and 15%, respectively) in comparison to Control and 1 nM CNP-22 (98% and 92%, respectively) (FIG. 1B). Due to the higher rate of GVBD oocytes observed with 10 and 100 nM CNP treatments, a follow up experiment was performed to explore the possibility of a slower process of meiotic resumption.

Figure 2:
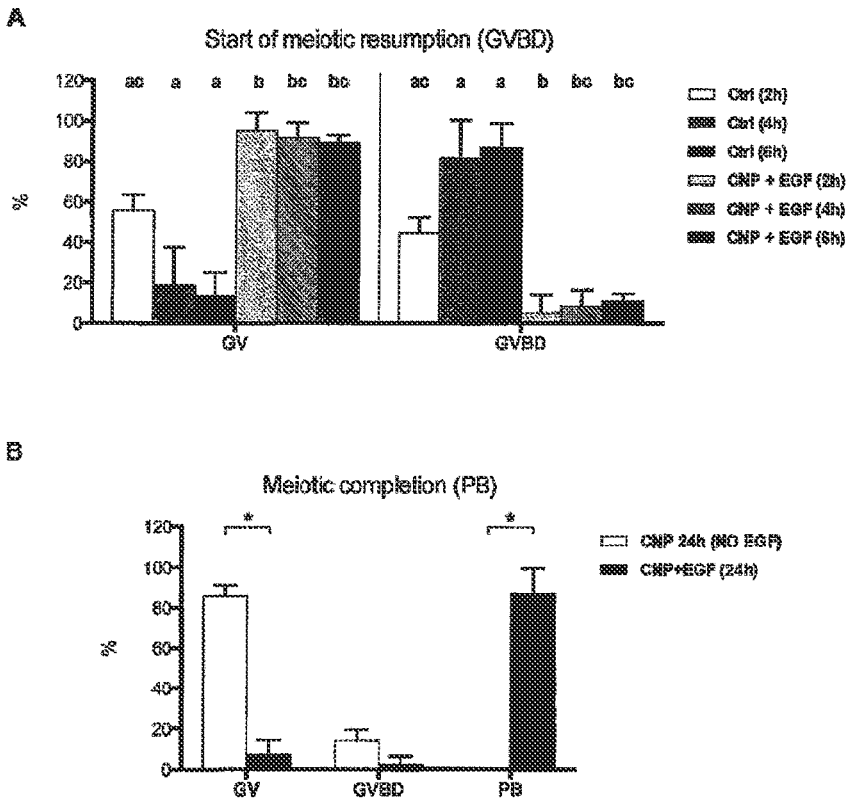
FIG. 2: CNP-22 delays EGFR-dependent reinitiation of meiosis (A) Pre-ovulatory COCs were placed in culture in presence of 0 (Control) or 25 nM CNP-22, 4 ng/ml. EGF, and early meiotic resumption was evaluated at 2, 4 and 6 hours after collection. (B) Pre-ovulatory COCs were placed in culture in presence of 25 nM CNP-22 or 25 nM CNP-22, 4 ng/ml. EGF, and meiotic maturation (meiotic completion up to PB extrusion) was evaluated 24 hours later. Each bar represents mean±SD of data obtained from three replicates (at least 41 oocytes/treatment). Different letters or a *indicate significant differences (P<0.05).

Pre-ovulatory COCs, retrieved from gonadotropin-primed mice, were placed in culture in absence (controls) or presence of 25 nM CNP-22 4 ng/mL EGF, and meiotic maturation was assessed at 2, 4 and 6 hours. While meiotic resumption increased from 2 to 6 hours in the control group, few GVBDs were induced in the CNP-22 EGF treated group (≤11%), within the same period of time (FIG. 2A). Additionally, COCs placed in CNP-22 EGF medium for 24 hours had a high occurrence of PB oocytes (93%), a figure significantly higher than in COCs cultured for the same period of time on CNP-22 only (FIG. 2B).

Altogether, these data suggests that CNP-22 is able to maintain meiotic arrest for at least 24 hours and that EGFR signaling is able to induce meiotic resumption in COCs kept under meiotic arrest by CNP, however at a slower pace (6 hours delay vs control).

Prolonged CNP-induced Meiotic Arrest of Immature COCs Relies on the Presence of Estradiol in the Culture Environment Similarly to the study described above; a replicate study with immature COCs (highly meiotically/developmentally incompetent) was performed. Such COCs were retrieved from small antral follicles (as described in M&M) and placed in culture for 48 hours. The results showed that CNP-22 can maintain meiotic arrest for 24 hours but not for 48 hours (data not shown), therefore, a study where responsiveness to CNP-22 is supported by medium supplementation with E2, FSH and GDF9 was designed.

Immature COCs were retrieved from small antral follicles of female mice aged 19-20 days-old and placed in culture for 48 hours in presence of 25 nM CNP-22 and presence or absence of 10 nM 17-β-estradiol; additionally the effects of the further addition of 2.5 or 5 [mIU/mL] *mIU/ml* FSH and/or 50 ng/mL GDF9 were evaluated.

Figure 3:
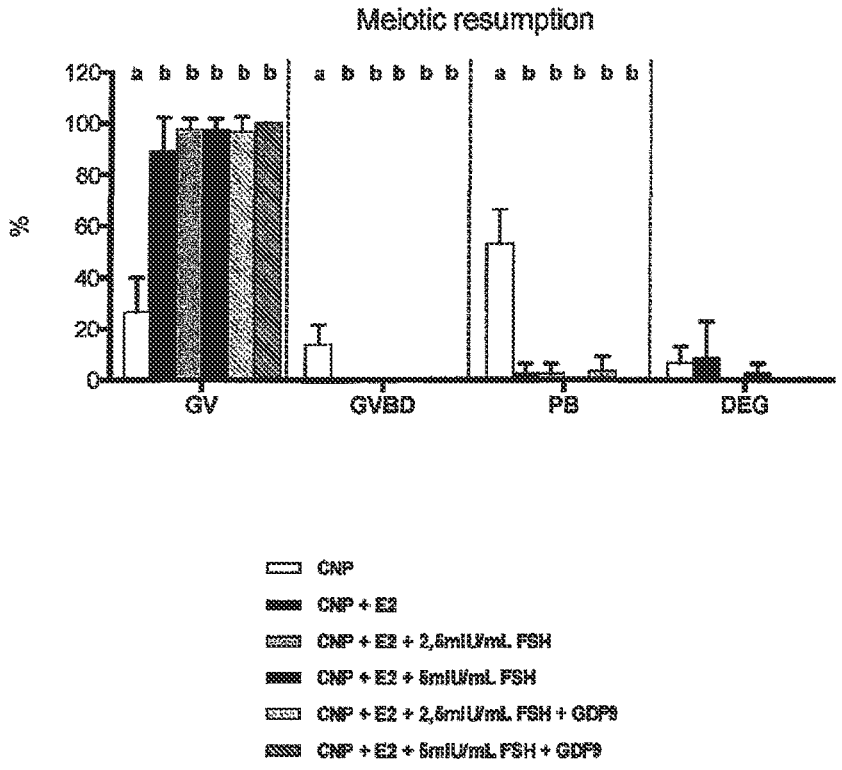
FIG. 3: Effects of E2, dose of FSH and GDF9 supplementation on oocyte meiotic arrest Immature COCs were placed in culture in presence of 25 nM CNP-22 alone or with 10 nM E2. Potential effects of adding [2,5 mIU/mL] *2.5 mIU/ml* or 5 [mIU/mL] *mIU/ml* FSH, alone or in combination with 50 ng/mL GDF9, on maintenance of meiotic arrest during 48 hours of culture, were evaluated. Each bar represents mean±SD of experimental data obtained from three replicates (at least 38 oocytes/treatment). Different letters indicate significant differences (P<0.05).

Oocytes of COCs cultured in presence of 25 nM CNP (alone) were predominantly unable to maintain meiotic arrest, consequently, after 48 hours of culture, the GV rate accounted for only 26% of the total number of COCs. In contrast, most of the oocytes of COCs cultured in presence of 25 nM CNP-22 plus 10 nM 17-β-estradiol (E2) were efficiently maintained in GV stage (≥89%; FIG. 3), regardless of a supplementation with FSH or GDF9.

Effects of FSH and GDF9 Supplementation on the State of the Oocyte Chromatin Condensation, Oocyte Diameter and COC Responsiveness to EGFR Ovulatory Signaling Immature COCs were retrieved from small antral follicles of female mice (aged 19-20 days-old), and placed in culture for 48 hours (Pre-IVM condition) in presence of 25 nM CNP-22 and 10 nM 17-β-estradiol and the addition of 2.5 [mIU/mL] *mIU/ml* FSH or [2,5mIU/mL] *2.5 mIU/ml* FSH +50 ng/mL GDF9. These pre-treatments were followed by 18 hours of ovulatory stimulus with medium containing EGF (IVM condition).

Figure 4:
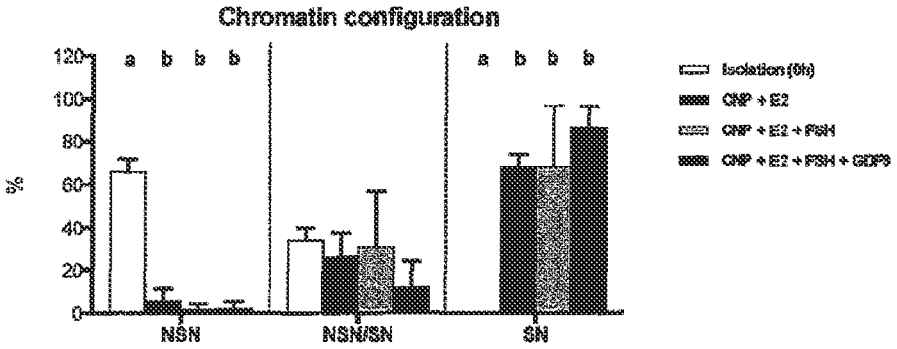
FIG. 4: Effects of a 48 hours culture period (Pre-IVM) on chromatin configuration and diameter of GV oocytes Immature COCs were placed in culture in presence of 25 nM CNP-22+10 nM E2. Potential supplementary effects of [2,5 mIU/mL] *2.5 mIU/ml* FSH or a combination of [2,5 mIU/mL] *2.5 mIU/ml* FSH+50 ng/mL GDF9, on oocyte's chromatin configuration (A) or oocyte's diameter (B), were evaluated. Chromatin configuration was assessed as described in material and methods and scored as NSN, NSN/SN (transitional) and NSN. Additionally, diameter was also assessed in oocytes immediately after isolation, prior to culture (0 h). In (A), each bar represents mean±SD of experimental data obtained from three replicates (at least 46 oocytes/treatment). In (B), at least 31 GV oocytes/treatment were measured. Different letters indicate significant differences (P<0.05).
Figure 4:
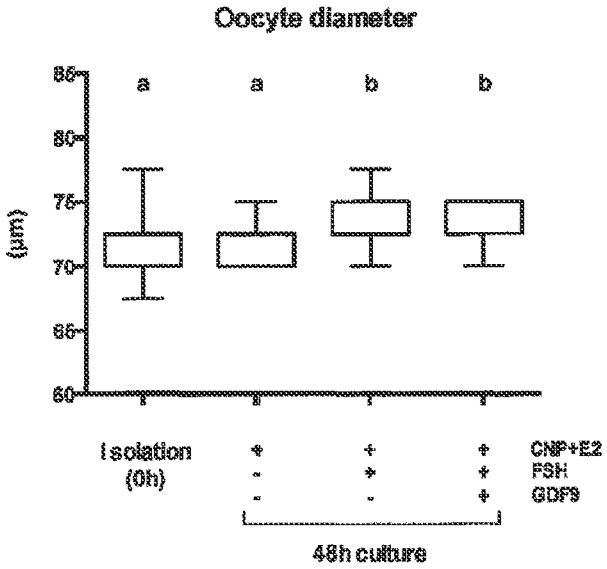

Analysis of oocyte's chromatin condensation before and after Pre-IVM treatment revealed that during 48 hours culture, oocyte's chromatin shifted from a predominant non-surrounded-nucleolus (NSN) disperse configuration to a surrounded-nucleolus (SN) condensed configuration. In fact, before Pre-IVM, 34% of the oocytes had the transitional NSN/SN configuration (66% NSN), white after Pre-IVM, ≥68% of the oocytes, in each of the conditions, displayed a SN pattern (FIG. 4A). A non-significant, but larger absolute amount of SN pattern (86%) was observed in oocytes cultured in presence of 2.5 [mIU/mL] *mIU/ml* FSH +50 ng/mL GDF9.

Additionally, oocytes obtained after Pre-IVM culture in FSH containing medium (w/o GDF9) reached a significantly larger mean diameter than oocytes cultured in medium without FSH. Consequently, immediately after isolation from the follicle (before Pre-IVM), oocytes displayed a diameter of 71.9±2.1 μm and following 48 hours of culture, oocyte diameters were as follows: 72.1±1.7 μm; 73.5±1.7 μm and 73.3±1.4 μm for CNP+E2, CNP+E2+FSH and CNP+E2+FSH+GDF9, respectively (FIG. 4B).

After Pre-IVM, some COCs were stimulated for meiotic resumption with EGF and their PB rate was evaluated after 18 hours. Due to a delay in meiotic reinitiation by the presence of CNP in IVM medium (see earlier experiment: CNP efficiently maintains meiotic arrest and delays EGFR-dependent meiotic resumption); for practical reasons, in the current experiment CNP was omitted from the IVM medium. Oocytes from 3 culture conditions showed a high rate of meiotic resumption: the PB rate was 79%, 78% and 82% PB rate for CNP+E2, CNP+E2+FSH and CNP+E2+FSH+GDF9, respectively.

Pre-IVM in presence of CNP, FSH and GDF9 Improves oocyte and embryo quality

Developmental competence of oocytes undergoing a Pre-IVM, followed by an IVM culture period was studied. Oocytes were in vitro fertilized and embryos cultured up to Day 5. For this experiment EREG was used as meiotic trigger during the IVM phase and CNP and GDF9 were only added to Pre-IVM medium and omitted from the IVM medium. Following the pre-IVM and IVM culture periods, cumulus cells from all treatments demonstrated profuse expansion and mucification in response to EREG.

Figure 5:
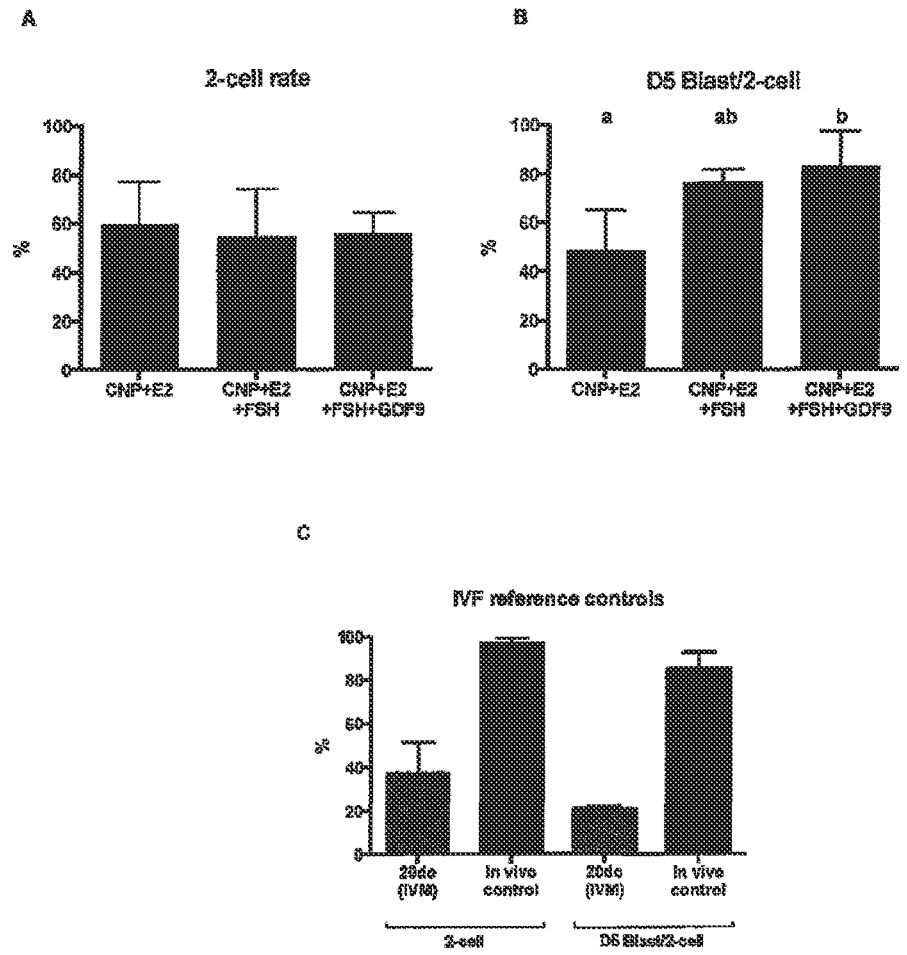
FIG. 5: Evaluation of oocyte and embryo quality following Pre-IVM+IVM

Two-cell (fertilization) rate was not different between the different treatments (60%, 54% and 58% for CNP+E2, CNP+E2+FSH and CNP+E2+FSH+GDF9, respectively). In comparison to the CNP+E2 condition, the rate of Day 5-blastocysts/2-cell was higher for oocytes cultured in medium containing FSH or FSH+GDF9; significantly for the latter (FIG. 5).

As reference, the competence of 1) Immature COCs undergoing IVM (without a Pre-IVM culture) and 2) In vivo grown oocytes after ovarian hyperstimulation with eCG followed by hCG, is displayed in FIG. 5C.

Example 2

The foregoing experiments show that the use of a capacitation medium according to the invention not only maintains oocytes under meiotic arrest, but does so without affecting the competence of such COCs to undergo IVM. However, CNP's action cannot be considered exclusively as having its action via effect upon phosphodiesterases (PDEs, the enzymes responsible for the degradation of cAMP within the oocyte during meiotic resumption); since oocyte developmental competence during the capacitation culture was greatly improved. Therefore, it was hypothesized that at low' doses CNP (in particular in the concentration range of 1 nM to 50 NM CNP) has a further (additional) effect in improving oocyte's developmental capacity by maintaining good communication between oocyte and cumulus cells.

In presence of cAMP modulators (specifically in pre maturation cultures using PDE3 inhibitors), a problem of disconnection between cumulus-corona and oocyte in long-term cultures has been clearly reported as a limitation of the PDE inhibitor method, when culturing COCs (Nogueira et al., 2003, Nogueira et al., 2006, Vanhoutte et al., 2009a).

To demonstrate that the Capacitation medium containing CNP actually sustains cumulus-oocyte connections, cumulus-oocytes complexes (COCs) from early antral follicles of the CBAB6F1 mice (supra), were placed in a basal culture medium for the culture of COCs and exposed to CNP and two well-known phosphodiesterase inhibitors, PDE3-I (Org9935 and Cilostamide) as comparators.

Materials and Methods

Animal Model

Animals used for the current study were CBAB6F1 (F1 hybrids of C57B1/6j×CBA/ca). These animals were housed and bred following, the national legislation and with the consent of the ethical committee of the Vrije Universiteit Brussel (Project number: 14-216-1).

Culture of COCs

Basal culture medium for the culture of COCs (Pre-IVM and IVM phases) consisted of α-MEM, 2.5% FBS (both from Life Technologies, Gent, Belgium) and 5 ng/mL Insulin, 5 ug/mL Apo-Transferrin, 5 ng/mL Sodium selenite (All from Sigma, Schnelldorf, Germany). Capacitation medium consisted of basal medium supplemented with either 25 nM CNP or 1 μM Org9935 or 1 μM Cilostamide in combination with 10 nM E2 17-β-estradiol. CNP was obtained from Phoenix Europe (Karlsruhe, Germany), while Cilostamide was obtained from Enzo Life Sciences (Antwerpen, Belgium). Since the aim of the experiment was to make evident potential differences between CNP and PDE3-inhibitors, avoiding potential interference of FSH was crucial, therefore the latter was omitted from capacitation medium. When tested in the presence of FSH, the latter masked the effect of CNP on the connection between the oocyte and surrounding layers of cumulus cells, in having itself a contribution to said connection which is even apparent in the presence of a PDE3-inhibitor (data not shown).

Staining and Image Analysis

Transzonal projections (TZPs, membranous extensions from the granulosa cell that connect with the oocyte) were evidenced by fluorescently labelling F-actin with Texas Red-Phalloidin or Actin green™, and were visible as filaments going through the zona pellucida (arrow heads).

Results

While the three compounds were able to maintain oocyte meiotic arrest, CNP unexpectedly revealed to be a factor capable of preserving the transzonal projections essential for bi-directional communication between oocyte and surrounding layers of cumulus cells (FIGS. 6 & 7). In FIG. 7 average pixel intensity was used as a tool to quantify positive actin staining (TZP) going through zona pellucida. Image analysis was performed with Image) and consisted of calculating average pixel intensity on the Region Of Interest (ROI) outlined in between the oocyte and cumulus cells, in the area were zona pellucida is located. Following image analysis, it was observed that COCs exposed to CNP kept better the connectivity between oocytes and cumulus cells, via transzonal projections (TZPs). In FIG. 7(A), Org9935 was used as inhibitor for PDE3 and actin filaments were evidenced with Texas-red bound phalloidin; while in FIG. 7(B), Cilostamide was used as inhibitor for PDE3 and actin filaments were evidenced with Actin green™. The CNP and PDE3i groups were statistically compared using a Mann Whitney test with a P value for panel A of 0.0082 and a P value for panel B <0.0001.

Example 3

Where the foregoing results demonstrate that CNP enhances the connectivity between the oocytes and the cumulus cells in the COCs, the following results aimed to determine whether this would have an impact on the development competence of such COCs cultivated from early antral follicles. In this study the differential effects of CNP and PDE3I present during a capacitation culture on the developmental competence of mouse cumulus-enclosed oocytes from early antral follicles were evaluated. Since the aim of the experiment was to make evident potential differences between CNP and PDE3-inhibitors, avoiding potential interference of FSH was crucial; therefore also in this experiment the latter was omitted from the capacitation medium.

Set Up:

Immature cumulus-oocyte complexes were isolated from early antral follicles (from unstimulated 19-20 day-old mice). COCs were placed in basal culture medium for a period of 48 hours in presence of either CNP or Cilostamide (PDE3-Inhibitor); similar to example 2.

Two Reference Controls were Included:

1) A control condition where no capacitation culture is performed before IVM,

2) A standard in-vivo control, fully-grown mature oocytes from 26-27 day-old mice. These COCs were obtained by administration of 48 h PMSG followed by hCG to mice aged 23-24 days-old (IVF protocol).

Following the capacitation culture, COCs were matured in presence of Epidermal growth factor (EGF) and in-vitro fertilized. Post fertilization embryo development was evaluated.

Acquisition of oocyte competence under each condition was evaluated by their capacity to mature, fertilize (2-cell rate) and to produce good quality blastocyst (by day 5 of embryo culture).

Statistical Analysis

Differences in the rate of fertilization and blastocyst formation between CNP and Cilostamide groups were assessed by chi-square.

Results

While there was no difference observed on the fertilization rate of both treatments (see FIG. 8(A)), the amount of blastocyst formed per fertilized egg was significantly higher following capacitation culture in presence of CNP (see FIG. 8 (B)).

Conclusion of Examples 2 & 3

The observed unexpected differences on oocyte and embryo quality in these two complimentary studies comparing PDE Inhibitors and CNP can be attributed to CNP. These results suggest that CNP has actions extending beyond those mediated via Phosphodiesterase type 3 regulation. Besides inhibiting the action of PDE3, CNP increases the physical connectivity between oocytes and cumulus cells enhancing the acquisition of the factors essential for completing oocyte's final development (cytoplasmic maturation).

Example 4

In Example 1, it has been demonstrated that CNP-22 had a dose-dependent effect on the maintenance of meiotic arrest. In the following study extra experiments including a broader range of CNP ranges were performed.

Set Up:

The materials and methods used in this further example are accordingly in common with the materials and methods used in Example 1. Cumulus-oocyte complexes from 24-26 day-old mice were isolated from in vivo grown antral follicles post 48 h equine Chronic Gonadotropin stimulation (eCG, Folligon, Intervet, Oss, The Netherlands). Mice were injected with 2.5 IU eCG when they were 22-24 days-old. Intact COCs with at least 2 layers of cumulus cells were put in culture for a period of 18 hours in presence of the following doses of CNP:

Control (No CNP)*

0.1 nM**

1 nM 10 nM 50 nM**

100 nM

1 μM**

*A control condition, in which CNP is not present in the culture media.

**0.1 nM, 50 nM and 1 μM new doses tested (included in the claims).

COCs were collected and cultured according to the previous dose experiments in mice, provided in the Example 1.

Statistical Analysis

Differences in the rate of oocyte meiotic resumption (per meiotic stage) were assessed by ANOVA followed by a Tukey's Multiple Comparison Test, $p<0.01$. Percentages data were transformed (arcsine) before performing statistical analysis.

Results:

In general, the current complementary experiments confirmed that CNP-22 had a dose-dependent effect on the maintenance of meiotic arrest. Oocyte meiotic arrest was confirmed by the presence of an intact germinal vesicle (GV) under the inverted microscope, FIG. 9A shows that doses from 1 nM, 10 nM, 50 nM and 100 nM maintain oocytes meiotic arrest at a rate ≥80% (80%, 98%, 94% and 87%, respectively). However, only doses of 10 nM and 50 nM were significantly higher compared to the control condition without CNP (98%, 94% vs. 50%, respectively, $p<0.01$).

No significant differences were recorded in the percentage of oocytes at the germinal vesicle breakdown (GVBD)-stage (FIG. 9B).

The low proportion or lack of oocytes extruding the first polar body (PB rate, FIG. 9C) at CNP doses of 1 nM, 10 nM, 50 nM and 100 nM (the three last ones being significant different compared to the control condition without CNP, $p<0.001$), matched the findings that at these doses CNP shows a more potent effect in the maintenance of oocyte meiotic arrest.

Unexpectedly, not only very low doses as 0.1 nM, but also very high doses as 1 μM demonstrated to be suboptimal in maintaining oocytes arrested at the GV stage.

Conclusion

Altogether, these data suggests that CNP-22 is able to maintain meiotic arrest in preovulatory oocytes at a rate above 80% at a dose interval ranging from 1 nM to 100 nM, and concur with the claim that a preferable dose of CNP to use in order to maintain all oocytes arrested at the GV stage would be 10-50 nM, more preferably a dose of 10-25 nM. As such this behaviour is different from the use of PDE3 inhibitors where increasing the doses did keep oocytes continuously arrested.

Example 5

In order to support that the foregoing CNP effects are not limited to CNP-22 per se, an additional experiment was performed to test whether these effects can be reproduced by CNP analogues. An additional experiment was performed to test the effect of the CNP analogue: CNP-53. Similar to CNP-22, CNP-53 is one of the major endogenous forms of C-TYPE natriuretic peptide, containing a 53-amino acid sequence.

Set Up:

The materials and methods used in this further example are accordingly in common with the materials and methods used in Example 4 but for the use of CNP-53 instead. Cumulus-oocyte complexes from 24-25 day-old mice were isolated from in vivo grown antral follicles post 48 h eCG stimulation. Mice were injected with 2.5 IU eCG when they were 22-23 days-old. Intact COCs were put in culture for a period of 18 hours in presence of the following doses of CNP-53:

Control (No CNP)*

0.1 nM 1 nM 10 nM 50 nM 100 nM

1 μM

Control 25 nM CNP-22*

*Two control conditions were included: 1) 25 nM CNP-22 (standard dose known and used in previous experiments to maintain meiotic arrest), 2) a control condition where CNP is not present in the culture media.

Statistical Analysis

Differences in the rate of oocyte meiotic resumption (per meiotic stage) were assessed by ANOVA followed by a Tukey's Multiple Comparison Test, $p<0.001$. Percentages data were transformed (arcsine) before performing statistical analysis.

Results:

Similar to the results found in the complementary experiments using CNP-22, CNP-53 demonstrated to have an unexpected (maximal) dose-dependent effect on the maintenance of oocyte meiotic arrest.

FIG. 10A shows that CNP-53 doses of 1 nM, 10 nM, 50 nM and 100 nM maintain oocytes under meiotic arrest at a rate significantly higher compared to the control condition without CNP (66%, 98%, 72% and 69% vs. 18%, respectively; $p<0.001$) and comparable to CNP-22 control (75%, $p<0.01$).

No significant differences were recorded in the percentage of oocytes at the germinal vesicle breakdown (GVBD)-stage (FIG. 10B).

The proportion of oocytes extruding the first polar body (PB stage) at doses of 1 nM, 10 nM, 50 nM and 100 nM were significant different compared to the control condition without CNP ($p<0.001$) and matched the findings that at these specific doses CNP-53 shows a more potent effect in the maintenance of oocyte meiotic arrest (FIG. 10C).

Unexpectedly, not only very low doses as 0.1 nM, but also very high doses as 1 μM demonstrated to be suboptimal in maintaining oocytes arrested at the GV stage.

Conclusion:

Overall, these data indicates that comparable to CNP-22, CNP-53 is able to maintain meiotic arrest in preovulatory oocytes at a high rate. Moreover, the doses at which CNP-53 is efficient are similar to those of CNP-22: 1 nM, 10 nM, 50 nM and 100 nM, expressed differently in a range of 1 nM to 100 nM CNP; with an optimal in a dose range of 10 nm to 50 nM to maintain meiotic arrest in all preovulatory oocytes.

Example 6

That the capacitation medium of the instant invention has indeed unexpected effects on the maturation of oocytes from small follicles follow from the results of a pre-clinical trail. In this study it has been assessed whether an IVM method using the capacitation medium of the instant application would have an effect on the oocyte developmental potential, on whether they produce fertilizable oocytes and on whether there is an increase in their blastocyst formation potential.

Patient Population:

Patients undergoing IVM treatment involved in the study (N=15) consented to donate a proportion of their oocytes for the generation of research embryos and had the following characteristics: age, <37 years old; clinical history of PolyCystic Ovary Syndrome (PCO or PCOS) according to the Rotterdam criteria (Rotterdam ESHRE/ASRM-Sponsored PCOS consensus workshop Group, 2004).

In case patients had 30 or more follicles at the last ultrasound scan prior to oocyte retrieval, a portion of these (usually between 5-10) were allocated to the New IVM Method; the rest were allocated to the routine clinical IVM protocol as part of patient treatment.

All patients received a personalized stimulation protocol consisting of a cumulative dose of 600 IU of HP-hMG (highly-purified human menopausal gonadotrophins, from Ferring Pharmaceuticals SA).

As soon as the patient demonstrated at least 1 leading follicle with average diameters in the range from 10-12 mm on ultrasound scan, tie ovum pick up (OPU) was planned 42 hrs after the last HP-hMG injection.

This Proof of Principle Study Recruited 15 Sibling Cases:

Experimental treatment=COC Capacitation (using the capacitation medium according to the invention)+IVM Routine clinical arm=Conventional IVM (Origio® IVM Methodology, VUB adapted)

Immature oocyte retrieval, Capacitation culture, IVM and ICSI

Cumulus-oocyte complexes (COCs) were retrieved from 2-10 mm follicles with a 17-gauge single-lumen needle at an aspiration pressure of 70 mmHg, and collected into "Collection medium" containing 50 μM IBMX (Sigma) supplemented with heparin at 25 IU/ml (Heparin Leo, Leo Pharma, Belgium).

Follicular aspirates at collection were instantaneously diluted in collection medium (3 ml prefilling of collection medium per tube). Contents of collection tubes were filtered from contaminating blood cells (Falcon cell strainer, 70 mm mesh size) and COCs were collected from the culture dish and held in collection media for a maximal time of 1 h. COCs were then washed and cultured at 37° C., 6% CO2 in air, in groups of maximally 10 COCs per well in 4-well IVF dishes (Nunc; Thermo Fisher Scientific; Denmark), each well containing 500 μl of "New Capacitation culture medium" with 25 nM CNP (i.e. a capacitation medium according to the invention).

After 22-26 hours of capacitation culture, COCs were thoroughly washed and transferred into IVM medium containing 100 ng/ml human recombinant Amphiregulin (rhAREG) and 100 [mIU/ml] *mIU/ml* recombinant FSH (Gonal-F), and incubated for 30 hours in same incubator conditions to allow in vitro meiotic maturation to occur.

Thirty hours post IVM culture, oocytes were mechanically and enzymatically freed from their cumulus layers under a stereomicroscope by using hyaluronidase (Cook Medical) and oocyte maturation was assessed under the inverted microscope.

Matured oocytes (PB extruded) involved in the research arm were microinjected with sperm from a common donor and embryo development was evaluated until Day 5 (and eventually Day 6) after ICSI.

Fertilization and embryo development were recorded at the standard assessment time points. Day 3 embryos with good morphology and considered to be transferable [based on the number of blastomeres (at least 5 cells), rate of fragmentation (maximum 20%), no evidence of multi-nucleation of the blastomeres, and/or early compaction] were classified as 'good quality embryos' (GQE).

Results:

FIGS. 11 and 12 are comparing the "NEW Capacitation culture+IVM" results with "routine IVM" on SIBLING OOCYTES, confronted to European ICSI data (from normally stimulated cycles) and routinely applied IVM at UZBrussel (2014-2015).

The first data set (Regular ICSI (Megaset)) are published conventional routine ICSI results in 374 patients superovulated with HP-hMIG and having had their oocytes collected from large follicles (Megaset® Study : (Source: Devroey et al. Fertil Steril 2012 Mar; 97(3):561-71)

The second [date] *data* set (Conventional IVM (Origio)) are UZBrussel data from 413 patients that underwent conventional IVM treatments using Origio® IVM media.

The Final and third data set (COC capacitation+IVM) are results from "NEW Capacitation culture+IVM" (method of the instant patent application) compared to their sibling oocytes treated with the Origin® IVM media.

The application of Capacitation Culture Method (i.e. a capacitation medium according to the invention). prior to human IVM, indicated important benefits for the culture of immature COCs: higher nuclear maturation rates and higher good quality Day 3 embryo and blastocyst Arrow (1) in FIG. 11, shows that the oocyte maturation rates are highly improved in comparison to conventional IVM. Arrow (2) in FIG. 11, shows that the fertilization rates are equal to regular ICSI cycles or conventional IVM. Arrow (3) in FIG. 11, shows that the yield of Good Quality Embryos on Day 3 (GQE D3) per number of initial COCs, is almost double as high than in conventional NM, comparable the rate of Good Quality Embryos obtained from mature oocytes from large follicles ICSI cycles.

Arrow (4) in FIG. 12 is referring to the yield of Good Quality Blastocysts on Day 5 or 6 of culture, either per number of fertilized eggs (2PN) or per [MII] *MII* oocytes. Results from "Capacitation Culture" are slightly higher than from conventional IVM. However, the fact that conventional IVM blastocysts are grown further only if the Day 3 embryology is favourable (4 or more excellent embryos at Day 3) affects those results positively. Therefore, when the same approach is applied to CNP (dotted white bar) results are by far superior to any of the other groups.

Arrow (5) in FIG. 12 is referring to the yield of Good Quality Blastocysts on Day 5 or 6 of culture, per number of initial COCs, in CNP group, are higher than conventional IVM (despite the positive selection bias in that group) and more comparable to regular ICSI cycles. Again the policy of ≥4 GQE on Day 3 applied to CNP group yields the best results among all groups.

Conclusion

The application of "New Capacitation Culture" culture step as part of the IVM treatment enhances the maturation of oocytes from small follicles up to a degree similar to in-vivo grown oocytes (obtained from large follicles after stimulation). The effects of this higher maturation are sustained during early embryogenesis, leading to a double amount of good quality embryos compared to conventional IVM. Achievement of such a sustained effect during early embryogenesis was beyond expectation and creates a flexible IVM method when compared to the currently used IVM methods.

The invention claimed is:

1. A capacitation medium for in vitro maturation of an immature mammalian cumulus oocyte complex, the *capacitation* medium comprising [0.1-50 nM] *from 0.1 nM to 100 nM* C-type natriuretic peptide (CNP), estradiol[and], Follicle Stimulating Hormone (FSH) *or an FSH analog, and from 0.1 ng/ml to 10 ng/ml insulin*.

[2. The capacitation medium according to claim 1, wherein said medium also comprises 0.1-10 ng/ml insulin.]

3. The capacitation medium according to claim 1, [wherein said medium] further [comprises] *comprising* an oocyte-secreted factor *or combination of oocyte-secreted factors*.

[4. The capacitation medium according to claim 1, wherein said medium comprises an oocyte-secreted factor selected from the group consisting of GDF-9, BMP-15, FGF-8, and combination thereof.]

[5. A kit for in vitro maturation of an immature mammalian cumulus oocyte complex, the kit comprising the capacitation medium according to claim 1.]

*6. The capacitation medium according to claim 1, comprising from 1 nM to 1000 nM estradiol.*

*7. The capacitation medium according to claim 1, comprising from 0.1 mIU/ml to 10 mIU/ml FSH or FSH analog.*

*8. The capacitation medium according to claim 1, further comprising from 10 ng/ml to 100 ng/ml oocyte-secreted factor.*

*9. The capacitation medium according to claim 8, wherein the oocyte-secreted factor is selected from the group consisting of GDF-9, functional equivalents or fragments of GDF-9, BMP-15, functional equivalents or fragments of BMP-15, FGF-8, functional equivalents or fragments of FGF-8, and combinations thereof.*

*10. A capacitation medium, comprising:*

*from 0.1 nM to 100 nM CNP;*

*from 1 nM to 1000 nM estradiol;*

*from 0.1 mIU/ml to 10 mIU/ml FSH or FSH analog;*

*from 0.1 to 10 ng/ml insulin; and*

*from 10 ng/ml to 100 ng/ml of an oocyte-secreted factor or combination of oocyte-secreted factors.*

*11. The capacitation medium according to claim 10, comprising from 10 nM to 100 nM CNP.*

*12. The capacitation medium according to claim 10, comprising from 0.1 nM to 50 nM CNP.*

*13. The capacitation medium according to claim 10, comprising from 10 nM to 50 nM CNP.*

*14. The capacitation medium according to claim 10, wherein the oocyte-secreted factor is selected from the group consisting of GDF-9, functional equivalents or fragments of GDF-9, BMP-15, functional equivalents or fragments of BMP-15, FGF-8, functional equivalents or fragments of FGF-8, and combinations thereof.*

*15. The capacitation medium according to claim 10, wherein the oocyte-secreted factor is selected from the group consisting of GDF-9, BMP-15, FGF-8, and combinations thereof.*

*16. A kit for in vitro maturation of an immature mammalian cumulus oocyte complex, the kit comprising the capacitation medium according to claim 1.*

*17. The kit according to claim 16, further comprising:*

*a collection medium;*

*a maturation medium;*

*non-adherent and/or adherent culture plates; and*

*instructions for use of the kit.*

*18. The capacitation medium according to claim 3, wherein the oocyte-secreted factor or combination of oocyte-secreted factors is selected from the group consisting of GDF-9, functional equivalents or fragments of GDF-9, BMP-15, functional equivalents or fragments of BMP-15, FGF-8, functional equivalents or fragments of FGF-8, and combinations thereof.*

* * * * *